United States Patent
Green et al.

(10) Patent No.: US 8,109,969 B1
(45) Date of Patent: *Feb. 7, 2012

(54) SYSTEM AND METHOD FOR ATTACHING SOFT TISSUE TO BONE

(75) Inventors: Michael L. Green, Pleasanton, CA (US); Joseph C. Tauro, Brick, NJ (US); Bart Bojanowski, San Jose, CA (US)

(73) Assignee: KFx Medical Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/245,622

(22) Filed: Sep. 26, 2011

Related U.S. Application Data

(60) Continuation of application No. 12/549,105, filed on Aug. 27, 2009, which is a division of application No. 11/143,007, filed on Jun. 1, 2005, now Pat. No. 7,585,311.

(60) Provisional application No. 60/576,477, filed on Jun. 2, 2004, provisional application No. 60/610,924, filed on Sep. 17, 2004, provisional application No. 60/634,174, filed on Dec. 7, 2004.

(51) Int. Cl.
*A61B 17/04* (2006.01)

(52) U.S. Cl. ......................... 606/232; 606/300

(58) Field of Classification Search .......... 606/72, 606/75, 78, 219, 224, 232, 300–331
See application file for complete search history.

(56) References Cited

U.S. PATENT DOCUMENTS

| | | | |
|---|---|---|---|
| 3,623,192 A | 11/1971 | Button | |
| 4,210,148 A | 7/1980 | Stivala | |
| 4,532,926 A | 8/1985 | O'Holla | |
| 4,796,612 A | 1/1989 | Reese | |
| 4,898,156 A | 2/1990 | Gatturna et al. | |
| 5,013,316 A | 5/1991 | Goble et al. | |
| 5,192,303 A | 3/1993 | Gatturna et al. | |
| 5,219,359 A | 6/1993 | McQuilkin et al. | |

(Continued)

FOREIGN PATENT DOCUMENTS
SU 1600713 10/1990
(Continued)

OTHER PUBLICATIONS

Arthrex, Inc.'s Answer to Plaintiff KFX Medical Corp.'s complaint for Patent Infringement and Counterclaims, United States District Court, Southern District of California, Sep. 23, 2011, Los Angeles, USA.

(Continued)

*Primary Examiner* — Darwin Erezo
*Assistant Examiner* — Gregory Anderson
(74) *Attorney, Agent, or Firm* — Knobbe Martens Olson & Bear LLP

(57) ABSTRACT

Disclosed herein are methods and devices for securing soft tissue to a rigid material such as bone. A bone anchor is described that comprises a base and a top such that suture material may be compressed between surfaces on the base and top to secure the suture to the anchor. Also described is an inserter that can be used to insert the bone anchor into bone and move the anchor top relative to the anchor base to clamp suture material there between. Also described is a soft-tissue and bone piercing anchor and associated inserter. Methods are described that allow use of the bone anchors to provide multiple lengths of suture material to compress a large area of soft tissue against bone.

17 Claims, 24 Drawing Sheets

U.S. PATENT DOCUMENTS

| | | |
|---|---|---|
| 5,224,946 A | 7/1993 | Hayhurst et al. |
| 5,269,784 A | 12/1993 | Mast |
| 5,336,240 A | 8/1994 | Metzler et al. |
| 5,372,604 A | 12/1994 | Trott |
| 5,417,712 A | 5/1995 | Whittaker et al. |
| 5,423,858 A | 6/1995 | Bolanos et al. |
| 5,423,860 A | 6/1995 | Lizardi et al. |
| 5,472,452 A | 12/1995 | Trott |
| 5,478,353 A | 12/1995 | Yoon |
| 5,500,001 A | 3/1996 | Trott |
| 5,527,341 A | 6/1996 | Gogolewski et al. |
| 5,527,343 A | 6/1996 | Bonutti |
| 5,543,012 A | 8/1996 | Watson et al. |
| 5,545,180 A | 8/1996 | Le et al. |
| 5,569,306 A | 10/1996 | Thal |
| 5,575,801 A | 11/1996 | Habermeyer et al. |
| 5,578,057 A | 11/1996 | Wenstrom, Jr. |
| 5,584,835 A | 12/1996 | Greenfield |
| 5,591,207 A | 1/1997 | Coleman |
| 5,634,926 A | 6/1997 | Jobe |
| 5,683,419 A | 11/1997 | Thal |
| 5,690,676 A | 11/1997 | DiPoto et al. |
| 5,697,950 A | 12/1997 | Fucci et al. |
| 5,720,765 A | 2/1998 | Thal |
| 5,725,557 A | 3/1998 | Gatturna |
| 5,769,894 A | 6/1998 | Ferragamo |
| 5,800,436 A | 9/1998 | Lerch |
| 5,814,072 A | 9/1998 | Bonutti |
| 5,891,168 A | 4/1999 | Thal |
| RE36,289 E | 8/1999 | Le et al. |
| 5,948,001 A | 9/1999 | Larsen |
| 5,948,002 A | 9/1999 | Bonutti |
| 5,951,590 A | 9/1999 | Goldfarb |
| 5,964,769 A | 10/1999 | Wagner et al. |
| 6,010,525 A | 1/2000 | Bonutti et al. |
| 6,013,077 A | 1/2000 | Harwin |
| 6,013,083 A | 1/2000 | Bennett |
| 6,027,523 A | 2/2000 | Schmieding |
| 6,045,573 A | 4/2000 | Wenstrom, Jr. et al. |
| 6,056,751 A | 5/2000 | Fenton, Jr. |
| 6,063,106 A | 5/2000 | Gibson |
| 6,093,201 A | 7/2000 | Cooper et al. |
| 6,093,301 A | 7/2000 | Van Atta |
| 6,099,547 A | 8/2000 | Gellman et al. |
| 6,110,207 A | 8/2000 | Eichhorn et al. |
| 6,117,160 A | 9/2000 | Bonutti |
| 6,117,161 A | 9/2000 | Li et al. |
| 6,126,677 A | 10/2000 | Ganaja et al. |
| 6,149,669 A | 11/2000 | Li |
| 6,200,330 B1 | 3/2001 | Benderev et al. |
| 6,241,749 B1 | 6/2001 | Rayhanabad |
| 6,245,082 B1 | 6/2001 | Gellman et al. |
| 6,280,474 B1 | 8/2001 | Cassidy et al. |
| 6,293,961 B2 | 9/2001 | Schwartz et al. |
| 6,296,659 B1 | 10/2001 | Foerster |
| 6,306,159 B1 | 10/2001 | Schwartz et al. |
| 6,319,271 B1 | 11/2001 | Schwartz et al. |
| 6,328,758 B1 | 12/2001 | Tornier et al. |
| 6,391,030 B1 | 5/2002 | Wagner et al. |
| 6,423,065 B2 | 7/2002 | Ferree |
| 6,432,123 B2 | 8/2002 | Schwartz et al. |
| 6,464,713 B2 | 10/2002 | Bonutti |
| 6,491,714 B1 | 12/2002 | Bennett |
| 6,514,274 B1 | 2/2003 | Boucher et al. |
| 6,518,200 B2 | 2/2003 | Lin |
| 6,520,980 B1 | 2/2003 | Foerster |
| 6,524,317 B1 | 2/2003 | Ritchart et al. |
| 6,527,794 B1 | 3/2003 | McDevitt et al. |
| 6,533,795 B1 | 3/2003 | Tran et al. |
| 6,540,770 B1 | 4/2003 | Tornier et al. |
| 6,547,800 B2 | 4/2003 | Foerster et al. |
| 6,551,330 B1 | 4/2003 | Bain et al. |
| 6,554,852 B1 | 4/2003 | Oberlander |
| 6,569,187 B1 | 5/2003 | Bonutti et al. |
| 6,575,987 B2 | 6/2003 | Gellman et al. |
| 6,582,453 B1 | 6/2003 | Tran et al. |
| 6,585,730 B1 | 7/2003 | Foerster |
| 6,605,096 B1 | 8/2003 | Ritchart |
| 6,635,073 B2 | 10/2003 | Bonutti |
| 6,638,279 B2 | 10/2003 | Bonutti |
| 6,641,597 B2 | 11/2003 | Burkhart et al. |
| 6,652,561 B1 | 11/2003 | Tran |
| 6,660,008 B1 | 12/2003 | Foerster et al. |
| 6,660,023 B2 | 12/2003 | McDevitt et al. |
| 6,673,094 B1 | 1/2004 | McDevitt et al. |
| 6,712,830 B2 | 3/2004 | Esplin |
| 6,770,076 B2 | 8/2004 | Foerster |
| 6,780,198 B1 | 8/2004 | Gregoire et al. |
| 6,855,157 B2 | 2/2005 | Foerster et al. |
| 6,984,241 B2 | 1/2006 | Lubbers et al. |
| 6,986,781 B2 | 1/2006 | Smith |
| 7,001,411 B1 | 2/2006 | Dean |
| 7,041,120 B2 | 5/2006 | Li et al. |
| 7,056,333 B2 | 6/2006 | Walshe |
| 7,081,126 B2 | 7/2006 | McDevitt et al. |
| 7,083,638 B2 | 8/2006 | Foerster |
| 7,090,690 B2 | 8/2006 | Foerster et al. |
| 7,144,415 B2 | 12/2006 | Del Rio et al. |
| 7,153,312 B1 | 12/2006 | Torrie et al. |
| 7,156,864 B2 | 1/2007 | Lintner |
| 7,232,455 B2 | 6/2007 | Pedlick et al. |
| 7,235,100 B2 | 6/2007 | Martinek |
| 7,247,164 B1 | 7/2007 | Ritchart et al. |
| 7,517,357 B2 | 4/2009 | Abrams et al. |
| 7,837,710 B2 | 11/2010 | Lombardo et al. |
| 8,029,537 B2 | 10/2011 | West, Jr. et al. |
| 2001/0008971 A1 | 7/2001 | Schwartz et al. |
| 2001/0018597 A1 | 8/2001 | Gellman et al. |
| 2001/0051815 A1 | 12/2001 | Esplin |
| 2001/0051816 A1 | 12/2001 | Enzerink et al. |
| 2002/0019649 A1 | 2/2002 | Sikora et al. |
| 2002/0029066 A1 | 3/2002 | Foerster |
| 2002/0077631 A1 | 6/2002 | Lubbers et al. |
| 2002/0111653 A1 | 8/2002 | Foerster |
| 2002/0128684 A1 | 9/2002 | Foerster |
| 2002/0169478 A1 | 11/2002 | Schwartz et al. |
| 2002/0188305 A1 | 12/2002 | Foerster et al. |
| 2003/0018358 A1 | 1/2003 | Saadat |
| 2003/0088270 A1 | 5/2003 | Lubbers et al. |
| 2003/0105591 A1 | 6/2003 | Hagiwara |
| 2003/0149448 A1 | 8/2003 | Foerster et al. |
| 2003/0167072 A1 | 9/2003 | Oberlander |
| 2003/0181925 A1 | 9/2003 | Bain et al. |
| 2003/0191498 A1 | 10/2003 | Foerster et al. |
| 2003/0195528 A1 | 10/2003 | Ritchart |
| 2003/0195563 A1 | 10/2003 | Foerster |
| 2003/0195564 A1 | 10/2003 | Tran et al. |
| 2003/0204204 A1 | 10/2003 | Bonutti |
| 2003/0236555 A1 | 12/2003 | Thornes |
| 2004/0002735 A1 | 1/2004 | Lizardi et al. |
| 2004/0024420 A1 | 2/2004 | Lubbers et al. |
| 2004/0044366 A1 | 3/2004 | Bonutti et al. |
| 2004/0093031 A1 | 5/2004 | Burkhart et al. |
| 2004/0098050 A1 | 5/2004 | Foerster et al. |
| 2004/0102779 A1 | 5/2004 | Nesper et al. |
| 2004/0116961 A1 | 6/2004 | Nesper et al. |
| 2004/0133238 A1 | 7/2004 | Cerier |
| 2004/0193217 A1 | 9/2004 | Lubbers et al. |
| 2004/0225325 A1 | 11/2004 | Bonutti |
| 2004/0243178 A1 | 12/2004 | Haut et al. |
| 2004/0254609 A1 | 12/2004 | Esplin |
| 2004/0267317 A1 | 12/2004 | Higgins et al. |
| 2005/0027307 A1 | 2/2005 | Schwartz et al. |
| 2005/0055052 A1 | 3/2005 | Lombardo et al. |
| 2005/0240199 A1 | 10/2005 | Martinek et al. |
| 2005/0240226 A1 | 10/2005 | Foerster et al. |
| 2005/0245932 A1 | 11/2005 | Fanton et al. |
| 2005/0283158 A1 | 12/2005 | West |
| 2005/0288682 A1 | 12/2005 | Howe |
| 2006/0067967 A1 | 3/2006 | Bowman et al. |
| 2006/0106423 A1 | 5/2006 | Weisel et al. |
| 2006/0116719 A1 | 6/2006 | Martinek |
| 2006/0161159 A1 | 7/2006 | Dreyfuss et al. |
| 2006/0178702 A1 | 8/2006 | Pierce et al. |
| 2006/0235413 A1 | 10/2006 | Denham et al. |
| 2006/0271060 A1 | 11/2006 | Gordon |
| 2006/0271105 A1 | 11/2006 | Foerster et al. |

| | | | |
|---|---|---|---|
| 2006/0293710 | A1 | 12/2006 | Foerster et al. |
| 2007/0142835 | A1 | 6/2007 | Green et al. |
| 2007/0142861 | A1 | 6/2007 | Burkhart |

FOREIGN PATENT DOCUMENTS

| | | | |
|---|---|---|---|
| WO | WO 99/52478 A1 | 10/1999 | |
| WO | WO 01/54586 A1 | 8/2001 | |
| WO | WO 01/67962 A2 | 9/2001 | |
| WO | WO 02/11630 A1 | 2/2002 | |
| WO | WO 02/21998 A1 | 3/2002 | |
| WO | WO 03/065904 A1 | 8/2003 | |
| WO | WO 2004/062506 A1 | 7/2004 | |
| WO | WO 2005/112786 A2 | 12/2005 | |
| WO | WO 2005/112788 A2 | 12/2005 | |
| WO | WO 2006/060035 A2 | 6/2006 | |
| WO | WO 2006/067548 A1 | 6/2006 | |
| WO | WO 2006/128092 A2 | 11/2006 | |
| WO | WO 2007/084714 A2 | 7/2007 | |

OTHER PUBLICATIONS

Complaint for Patent Infringement, dated Aug. 1, 2011, *KFX Medical Corporation v. Arthrex, Inc.,* (S.D.C.A.).

International Preliminary Report on Patentability dated Jan. 25, 2007 for International Application No. PCT/US2005/019454.

International Search Report and Written Opinion of the International Searching Authority, dated Sep. 6, 2006, for International Application No. PCT/US2005/019454.

Lo et al., Double-Row Arthroscopic Rotator Cuff Repair: Re-Establishing the Footprint of the Rotator Cuff, Arthroscopy: The Journal of Arthroscopic and Related Surgery, Nov. 2003, pp. 1035-1042, vol. 19, No. 9.

Mazzocca et al., Arthroscopic Single-Row Versus Double-Row Suture Anchor Rotator Cuff Repair, The American Journal of Sports Medicine, 2005, 33:1861.

Mazzocca et al., Arthroscopic Single versus Double Row Suture Anchor Rotator Cuff Repair, abstract of presentation made on Jun. 25, 2004 at 2004 Annual Meeting of the American Orthopaedic Society for Sports Medicine in Quebec, Canada, publication date unknown.

Millett et al., Mattress double anchor footprint repair: a novel, arthroscopic rotator cuff repair technique, Arthroscopy: The Journal of Arthroscopic and Related Surgery, 20(8):875-879 (2004).

Paulos, M.D., Graftjacket Regenerative Tissue Matrix Rotator Cuff, date unknown, Wright Medical Techology, Inc.; Wright Cremascoli Ortho SA, 2011.

PCT International Preliminary Report on Patentability, dated May 22, 2009, for International Application No. PCT/US2007/083662.

PCT International Search Report and Written Opinion, dated Aug. 8, 2008, for International Application No. PCT/US2007/083662.

PCT Invitation to Pay Additional Fees, dated May 13, 2008, for International Application No. PCT/US2007/083662.

Robbe, M.D. et al., Knotless Suture-based Anchors, Operative Techniques in Sports Medicine, 2004, pp. 221-224, Elsevier Inc.

Seldes, M.D., et al., Tissue Mend Arthroscopic Insertion of a Biologic Rotator Cuff Tissue Augment After Rotator Cuff Repair, Stryker, date unknown, pp. 1-7, 2006.

Statement of Tate Scott, dated Apr. 12, 2011, submitted in Re-Examination No. 90/011,430.

TissueMend Advanced Soft Tissue Repair Matrix, Stryker, date unknown, 2003.

TissueMend Soft Tissue Repair Matrix, Stryker, 2004, USA.

Waltrip, "Rotator Cuff Repair A Biomechanical Comparison of Three Techniques", The American Journal of Sports Medicine, 2003, pp. 493-497, No. 4.

Yian, M.D., et al., Arthroscopic Repair of SLAP Lesions With a Bioknotless Suture Anchor, Arthroscopy: The Journal of Arthroscopic and Related Surgery, May-Jun. 2004, pp. 547-551, vol. 20, No. 5. Arthroscopy Association of North America.

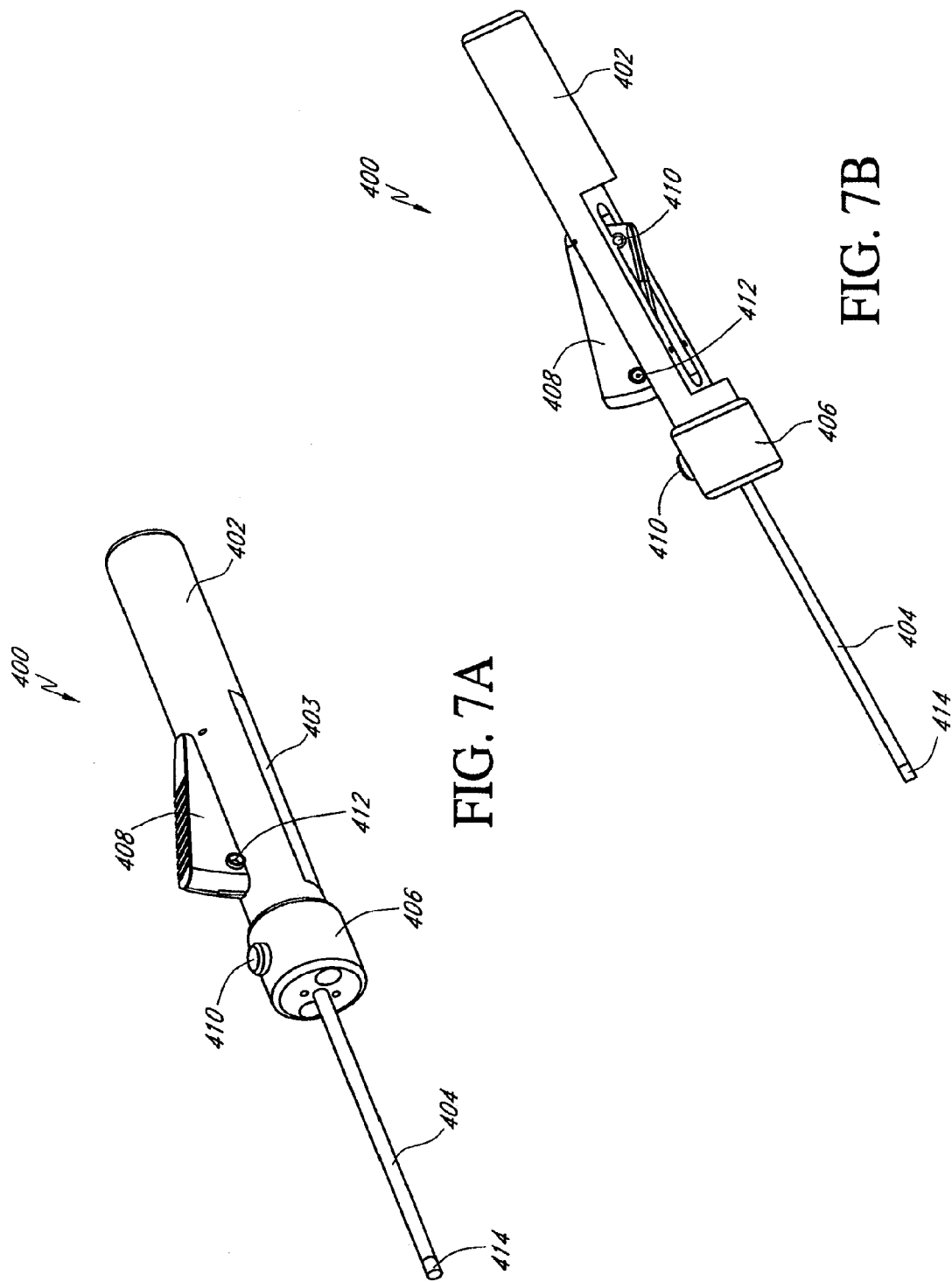

SYSTEM AND METHOD FOR ATTACHING SOFT TISSUE TO BONE

RELATED APPLICATIONS

This application is a continuation of U.S. application Ser. No. 12/549,105, filed Aug. 27, 2009, which is a divisional of U.S. application Ser. No. 11/143,007, now U.S. Pat. No. 7,585,311, filed Jun. 1, 2005, which claims priority to U.S. Provisional Application Nos. 60/576,477, filed on Jun. 2, 2004; 60/610,924, filed on Sep. 17, 2004; and 60/634,174, filed on Dec. 7, 2004; all of which are incorporated herein by reference in their entirety.

BACKGROUND OF THE INVENTION

1. Field of the Invention

The present invention relates to medical devices and procedures. More particularly, the present invention relates to devices and methods for securing soft tissue to a rigid material such as bone.

2. Description of the Related Art

There are several medical procedures where a surgeon needs to attach soft tissue such as tendons or other soft connective tissue to bone. One common example is a torn rotator cuff, where the supraspinatus tendon has separated from the humerus causing pain and loss of ability to elevate and externally rotate the arm. To repair a torn rotator cuff, typically a surgical procedure is used to suture the torn tendon to the bone using a variety of methods. Some procedures utilize large incisions and involve complete detachment of the deltoid muscle from the acromion. Small diameter holes are made in the bone for passing suture material through the bone to secure the tendon. Such large incision procedures are traumatic, causing prolonged pain and recovery time. Other procedures make small incisions and use arthroscopic techniques to attach sutures using either small diameter holes or a bone anchor. However, it is difficult to manipulate sutures within the surgical site using arthroscopic techniques. In addition, when knot tying is used to secure the suture to a bone anchor, it is difficult to properly adjust the tension of the suture while tightening the knot. Similarly, when the suture is attached to a bone anchor prior to insertion of the anchor into the bone, it is difficult to judge the appropriate point of attachment so that the suture will be properly tensioned upon insertion of the bone anchor into the bone. Thus, there is a need for methods and devices that allow easy arthroscopic attachment of a suture to a bone anchor after the anchor is inserted into the bone without the use of knot tying.

SUMMARY OF THE INVENTION

The present invention is particularly suited for use in arthroscopic procedures, including but not limited to rotator cuff surgery. More broadly, it can be used in any procedure in which it is desired to fix a suture to a solid object without tying of knots, including not only arthroscopic procedures, but also open surgery, and can be used for such diverse purposes as bladder neck suspension, tendon and ligament affixation or repair, prosthetic attachment, and rotator cuff repair.

In one embodiment, the invention includes an anchor for securing a suture to bone, including an anchor base adapted to be securely fixed into the bone and a suture securing mechanism coupled to the anchor base and positioned proximally relative to the anchor base, the mechanism adapted to receive and secure a suture moved laterally into the In another embodiment, the invention includes an anchor for securing a suture to bone, including an anchor base adapted to be securely fixed into the bone, a first surface coupled to the anchor base and positioned proximally relative to the anchor base, and a second surface coupled to the anchor base and positioned proximally relative to the anchor base, wherein the first and second surfaces are adapted to be relatively positioned in at least two configurations, one of the configurations such that a gap is present between the first and second surfaces so that the suture can be positioned between the first and second surfaces by moving the suture laterally into the gap, and the other of the configurations such that the first and second surfaces are in close proximity so that the suture can be securely clamped between the first and second surfaces.

In another embodiment, the invention includes a method of attaching soft tissue to bone, including passing a length of suture over the soft tissue, inserting an anchor into the bone, and securing the length of suture to the anchor after the inserting without passing an end of the length of suture through any aperture in the anchor and without tying any knots.

In another embodiment, the invention includes a method of attaching soft tissue to bone, including inserting a first anchor through the soft tissue, wherein the first anchor comprises a length of suture fixedly secured to the first anchor prior to insertion, inserting the first anchor into the bone, passing the length of suture over the soft tissue, and fixedly securing, after the passing, the length of suture to a second anchor.

In another embodiment, the invention includes a method of attaching soft tissue to bone, the soft tissue comprising a first surface adjacent to the bone's surface and a second surface opposite the first surface, the method including inserting a first portion of a length of suture into the second surface of the soft tissue, passing a second portion of the length of suture over the second surface of the soft tissue, inserting a first anchor with no suture coupled thereto into the bone, and fixedly securing the length of suture to the inserted first anchor, with the proviso that no part of the first portion of the length of suture is passed out of the second surface of the soft tissue.

In another embodiment, the invention includes a method of attaching soft tissue to bone, including inserting a first anchor with a length of suture pre-coupled thereto through the soft tissue, inserting the first anchor into the bone, inserting a second anchor with no suture coupled thereto into bone, passing the length of suture over the soft tissue, and fixedly securing the length of suture to the inserted second anchor.

In another embodiment, the invention includes a method of attaching soft tissue to bone, the method including inserting a first, second, and third anchor into the bone, fixedly securing a first length of suture over the soft tissue to the first and second anchors, and fixedly securing a second length of suture over the soft tissue to the first and third anchors.

In another embodiment, the invention includes an anchor for securing a suture to bone, the anchor including an anchor base adapted to be securely fixed into the bone, the anchor base comprising a first proximal surface and an anchor top, the anchor top comprising a distal member coupled to the anchor base and a first proximal member comprising a first distal surface, wherein the anchor top is adapted to couple to the anchor base in at least two configurations, one of the configurations such that the first distal surface is above the bone's surface when the anchor base is securely fixed into the bone, such that a suture can be freely passed between the first proximal and first distal surfaces above the bone's surface, and the other of the configurations such that the first distal surface is in close proximity to the first proximal surface, such that a suture can be securely clamped between the first proximal and first distal surfaces.

In another embodiment, the invention includes an anchor for securing a suture to bone, the anchor including a substantially hollow cylinder comprising an open end and comprising a portion of its walls cut in such a manner so as to allow the cylinder to deform under stress and form lateral protrusions, a substantially pointed tip coupled to the cylinder opposite the open end, wherein the pointed tip is adapted to pierce the bone, and a suture receiver coupled to the pointed tip and positioned within the substantially hollow cylinder so that a suture may be attached to the suture receiver and extend through the cylinder and out of the open end.

BRIEF DESCRIPTION OF THE DRAWINGS

FIG. 2 depicts attaching soft tissue to bone using a two bone anchors with a suture stretched there between.

FIGS. 7A and 7B depict a suture anchor inserter.

DETAILED DESCRIPTION OF THE CERTAIN EMBODIMENTS

Figure 1:
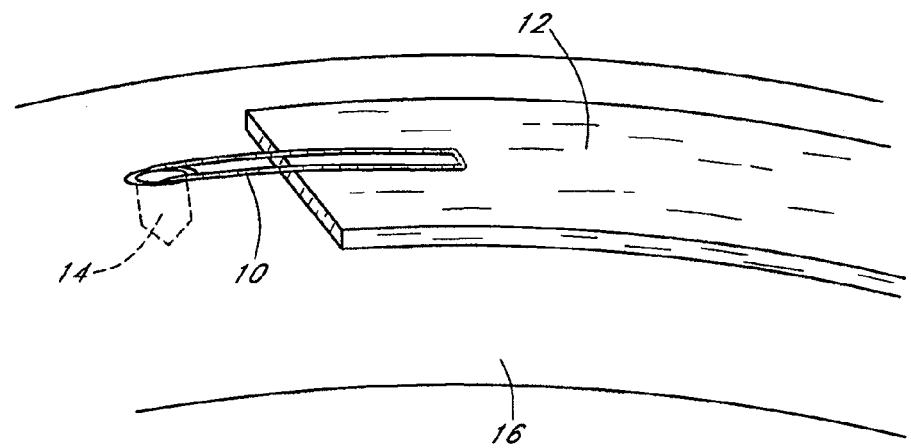
FIG. 1 depicts attaching soft tissue to bone using a single bone anchor and a stitch.

In various embodiments, soft tissue may be attached to bone utilizing one or more bone anchors with suture attached thereto. As used herein, "suture" refers to any flexible structure that can be stretched between two or more anchors and includes, without limitation, traditional suture material, single or multiple stranded threads, or a mesh structure. In some embodiments, suture is passed over the top of the soft tissue so that the suture can press the soft tissue against the bone. In one embodiment, a length of suture is attached to a single bone anchor. One non-limiting example, depicted in FIG. 1, includes stitching the suture 10 to the soft tissue 12, such as by an incline mattress stitch, and then securing the suture 10 to the single bone anchor 14 that is inserted into the bone 16. However, in other embodiments, a length of suture is attached to multiple bone anchors. The use of multiple bone anchors increases the footprint over which the suture material presses the soft tissue against bone. One non-limiting example, depicted in FIG. 2, includes two bone anchors. One anchor 20 is positioned in a medial location underneath the soft tissue 12 and a second anchor 22 is positioned lateral to the soft tissue 12. The suture 10 is attached to both anchors.

In one embodiment, the suture 10 is attached to the lateral bone anchor 22 only after the medial bone anchor 20 is inserted and the suture 10 is passed over the soft tissue 12. In one embodiment, the suture 10 is attached to the medial bone anchor 20 prior to insertion of the medial bone anchor 20. Thus, in this embodiment, the surgeon does not need to pass the suture through the soft tissue 12 from beneath the soft tissue 12. In one embodiment, the procedure involves inserting the medial bone anchor 20 with suture 10 pre-attached through the soft tissue 12. The medial bone anchor 20 may then be moved laterally relative to the bone 16 in order to pull the soft tissue 12 laterally relative to the bone 16. After appropriate positioning of the soft tissue 12, the medial bone anchor 20 may then be inserted into the bone 16. The lateral bone anchor 22 may then be inserted into the bone 16. The suture 12 may then be passed over the soft tissue 12 and attached to the lateral bone anchor 22. In some embodiments, a lateral bone anchor 22 is provided to which suture 12 can be attached without tying any knots or without passing the suture 12 through any aperture in the lateral bone anchor 22.

Figure 3A:
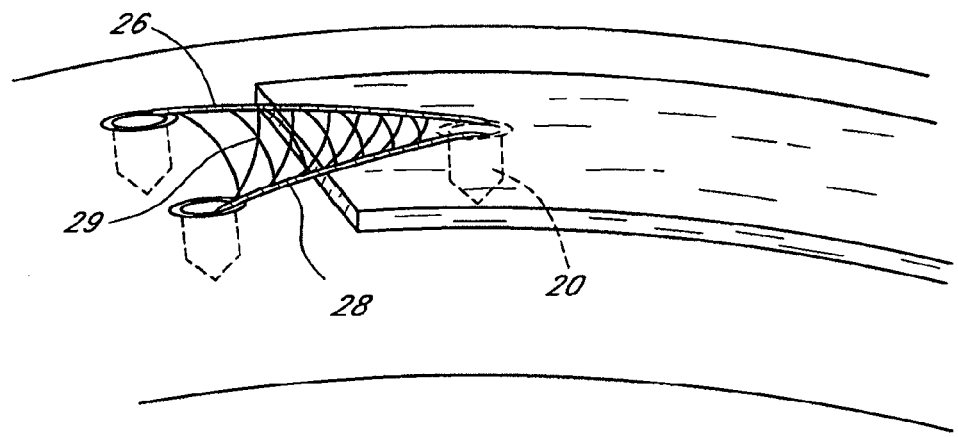
FIGS. 3A-3C depict various geometries of bone anchors and suture patterns for attaching soft tissue to bone.
Figure 3B:
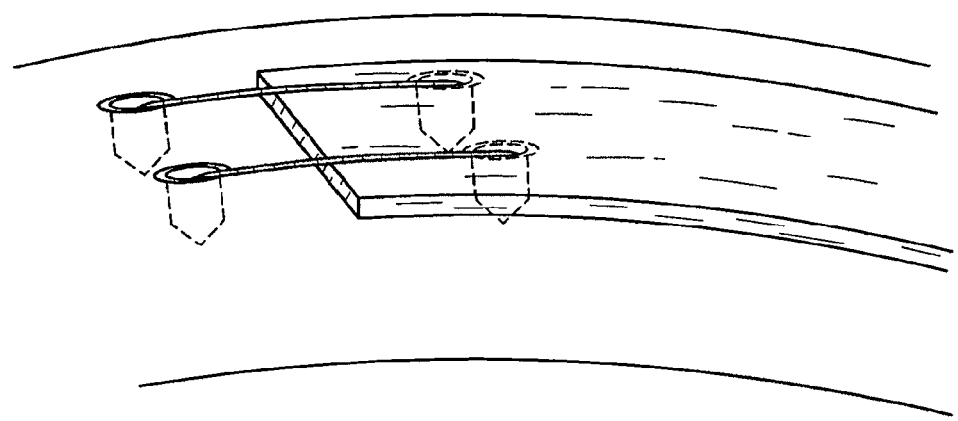
Figure 3C:
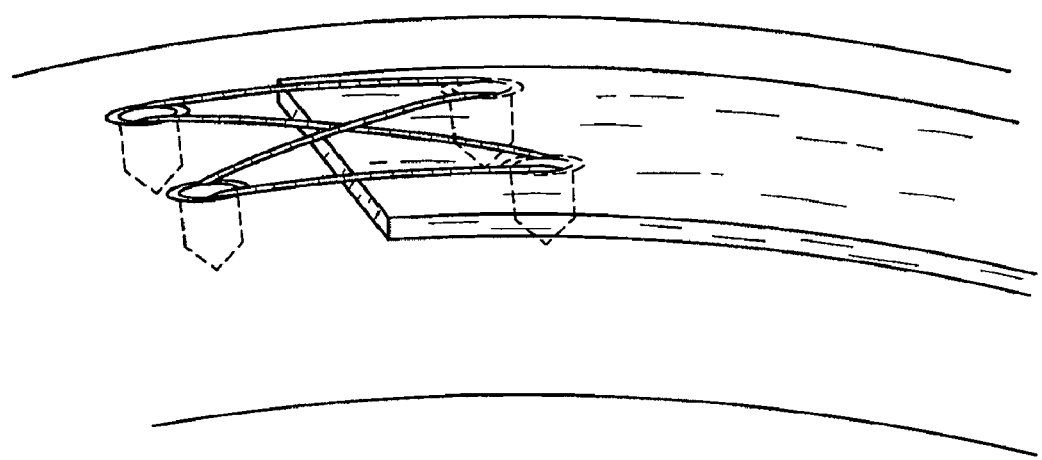

In some embodiments, multiple anchors and multiple suture lengths may used to provide a wider area of pressure of the soft tissue against bone. For example, as depicted in FIG. 3A, three anchors are used with two lengths of suture 26 and 28. Alternatively, a mesh structure 29 may be stretched between the three anchors. In another example, as depicted in FIG. 3B, four anchors are used with two lengths of suture. In still another example, as depicted in FIG. 3C, four anchors are used with four lengths of suture. In some embodiments, the individual suture lengths may be part of a larger continuous suture. For example, in FIG. 3A, the suture lengths 26 and 28 may be part of a larger length of suture such that the lengths 26 and 28 are joined at medial bone anchor 20. Those of skill in the art will appreciate that there are any number of anchor and suture geometries that can be used.

In some embodiments, the medial bone anchors 20 are designed so that they can be easily pierced through the soft tissue 12 and bone 16. In some embodiments, the lateral bone anchors 22 are designed so that they can easily capture suture material after insertion of the bone anchors 22. Together, these design features provide a suturing system and method that provides an increased footprint of suture pressure against the soft tissue 12 and ease of implementation for a surgeon. For example, in some embodiments, the entire procedure may be done arthroscopically, with the surgeon needing only to insert the medial bone anchor 20 with suture optionally pre-attached through a first port, insert the lateral anchor 22 through a second port, pass the suture over the soft tissue 12 by capturing it from within the second port, and securing the suture to the lateral anchor 22. Accordingly, described below are certain embodiments of anchors adapted to capture suture material and anchors adapted to easily pierce through soft tissue and bone.

Suture Capturing Anchor

One embodiment is a bone anchor that allows easy capturing and securing of a suture after the bone anchor is inserted into the bone. In one embodiment, the bone anchor includes a suture securing mechanism positioned on the proximal end of the bone anchor (i.e., the end nearest the surface of the bone and the surgeon). In one embodiment, the suture securing mechanism allows a suture to be moved laterally into the mechanism. By "laterally," it is meant that the suture can be moved into the mechanism by moving the suture in a direction that is generally perpendicular to the axis of the suture. In other words, the suture can be moved into the mechanism without threading an end of the suture into the mechanism. In one embodiment, the suture can be fixedly secured within the mechanism without tying any knots. By "fixedly secured," it is meant that the suture within the securing mechanism cannot be easily moved relative to the bone anchor.

One embodiment is a bone anchor that allows easy attachment of suture material by clamping the suture material between two surfaces on the bone anchor. The bone anchor may be configured such that the bone anchor is inserted into the bone without the suture material attached. The two surfaces of the suture securing mechanism may be spaced apart so as to form a gap between the surfaces. The suture material may be passed between the two surfaces and tensioned as desired followed by clamping of the two surfaces together, thereby clamping the suture material there between.

In one embodiment, the bone anchor consists of two parts: an anchor base and an anchor top. The anchor base may be designed to be inserted into a hole in the bone with a proximal surface facing up. The anchor top may be coupled to the anchor base via a distal member. A proximal member on the anchor top may have a distal surface facing down toward the proximal surface on the anchor base. The coupling of the anchor top to the anchor base may be such that the anchor top can move relative to the anchor base such that it can be positioned in one configuration where there is space between the proximal surface on the anchor base and the distal surface on the proximal member of the anchor top. In another configuration, the proximal member of the anchor top may be position such that there is very little space, if any, between the proximal surface on the anchor base and the distal surface on the proximal member of the anchor top. Thus, in the first configuration, suture material may be easily passed between the two surfaces and tensioned as desired. In the second configuration, the suture material may be clamped between the two surfaces such that the suture is secured to the bone anchor.

Figure 4A:
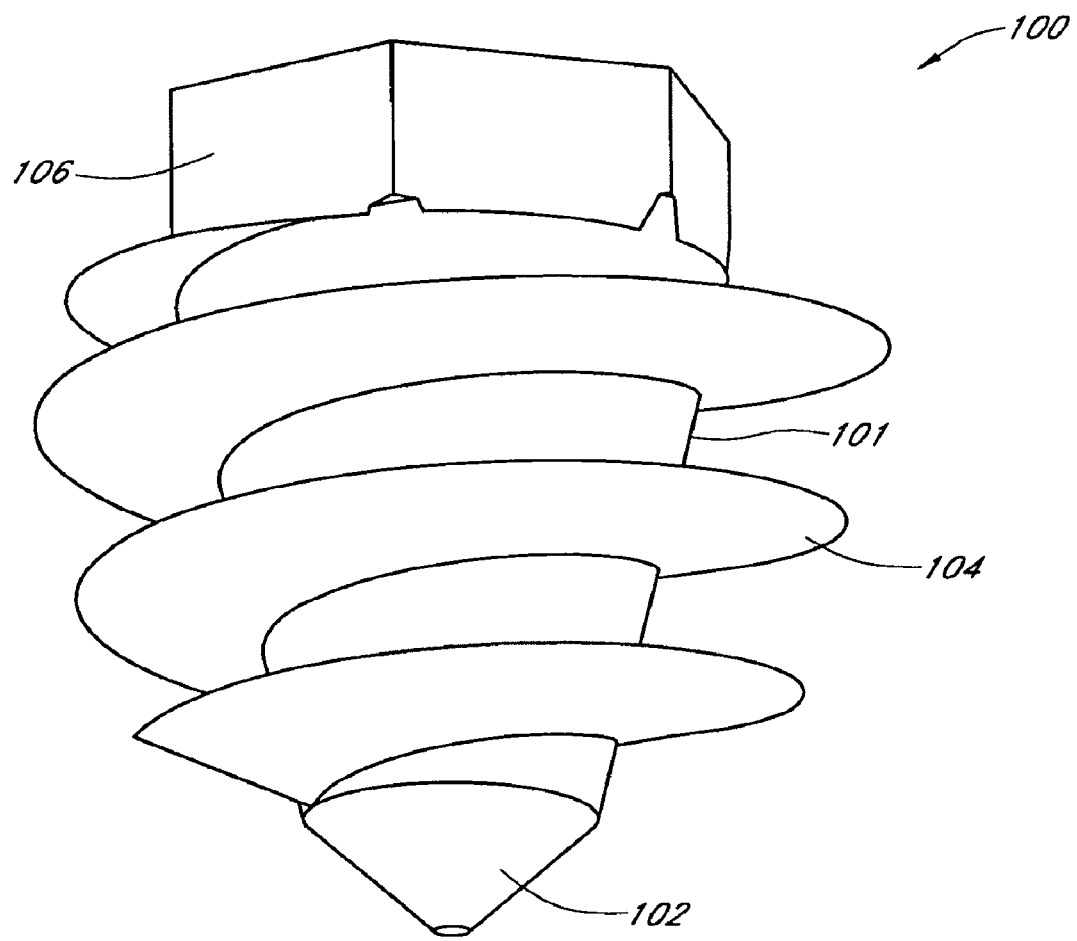
FIGS. 4A-4D depicts the base of a two-part suture anchor that can be inserted into bone.

One embodiment of an anchor base 100 is depicted in FIGS. 4A through 4D. FIG. 4A is a perspective view showing the side 101 and bottom 102 of the anchor base 100. The bottom 102 of the anchor base 100 may advantageously be tapered to facilitate insertion of the anchor base 100 into bone. In some embodiments, a hole is predrilled into the bone to facilitate insertion of the anchor base 100. In other embodiments, the anchor base 100 is forced directly into the bone, thereby creating the hole. The sides 101 of the anchor base 100 comprise threads 104 so that the anchor base 100 may be inserted into bone using a screwing action. In some embodiments, the anchor base 100 may be tapped to start the threads 104 into the bone followed by screwing the anchor base 100 into the bone. When the hole in the bone is pre-drilled, the hole is advantageously drilled with a diameter smaller than the diameter of threads 104 so that the threads engage the bone through the sides of the hole. It will be appreciated that means other than threads may be used to secure the anchor base 100 to bone. For example, angled protrusions may be used that provide greater resistance to removal of the anchor base 100 than to insertion. The protrusions may be static or deployable once the anchor is inserted.

The top of anchor base 100 preferably includes a structure 106 for facilitating the driving or screwing of the base 100 into the bone. In the illustrated embodiment, this comprises a hex nut structure 106 that facilitates engagement with a hex nut driver for screwing the anchor base 100 into the bone. It will be appreciated that other structures known in the art for engaging tools used for screwing action may be used instead of hex nut structure 106, and that this structure can be indented into or extending out from the top of the anchor base 100, or can alternatively be formed on the sides of the anchor base 100.

Figure 4B:
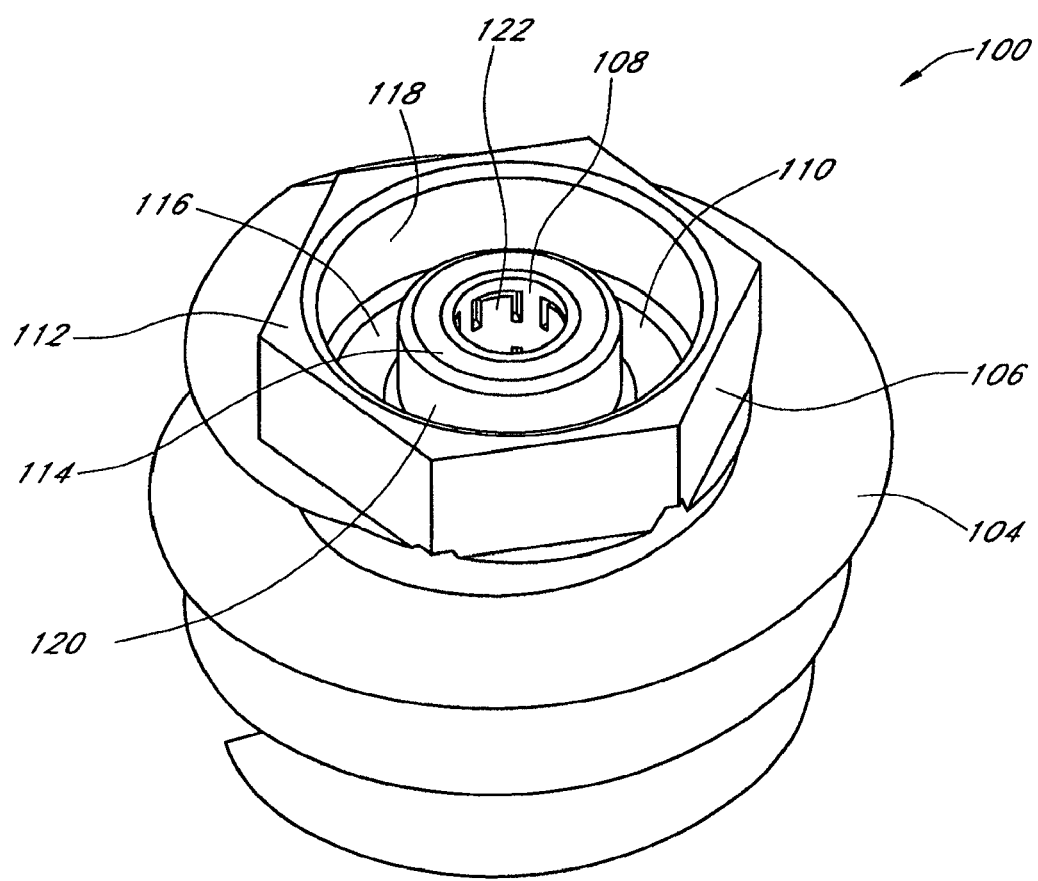

With reference to FIG. 4B, which is a perspective view of the top and side of anchor base 100, the top (proximal end) comprises a hole 108 in the center for receiving the anchor top, which is described below. The top of anchor base 100 also contains a suture gripping structure such as a circular groove 110 that may be concentric with hole 108. Because of groove 110, the proximal surface of anchor base 100 is not flat and comprises top surfaces 112 and 114, bottom surface 116, and side surfaces 118 and 120. In some embodiments, some or all of these surfaces may be textured such as with a scallop shape or grooves so as to inhibit movement of suture material pressed against the surfaces. Although a grooved surface is illustrated, it will be appreciated that other shapes for the proximal surface of anchor base 100 are also contemplated, including multiple concentric grooves, a series of protruding ridges, a "vee" shaped channel, or any other suitable structure that permits a suture to be securely locked against the top or proximal end of the anchor base 100.

Hole 108 in anchor base 100 is an opening into a central ("axial") bore into the anchor base 100. The sides of the central bore preferably include structures for gripping something inserted into the central bore, such as ratchet structures 122. FIG. 4C show a central ratchet bushing 126 that fits within the central bore and contains the ratchet structures 122. In the embodiment of FIG. 4C, the ratchet structures 122 are constructed by cutting U shaped cuts into bushing 126. The U shaped cuts then define tabs that make up the ratchet structures 122. It will be appreciated that other shapes and methods for making ratchet structures may be used. The purpose of ratchet bushing 126 is to receive the anchor top and secure it to the anchor base 100. It will be appreciated that other methods of securing the anchor top to the anchor base 100 may be used, such as a frictional fit or threading. Furthermore, the anchor top may be coupled to the anchor base 100 using means other than hole 108 and bushing 126. For example, the anchor top may be coupled via structures at the perimeter rather than the center or by a hinge.

Figure 4D:
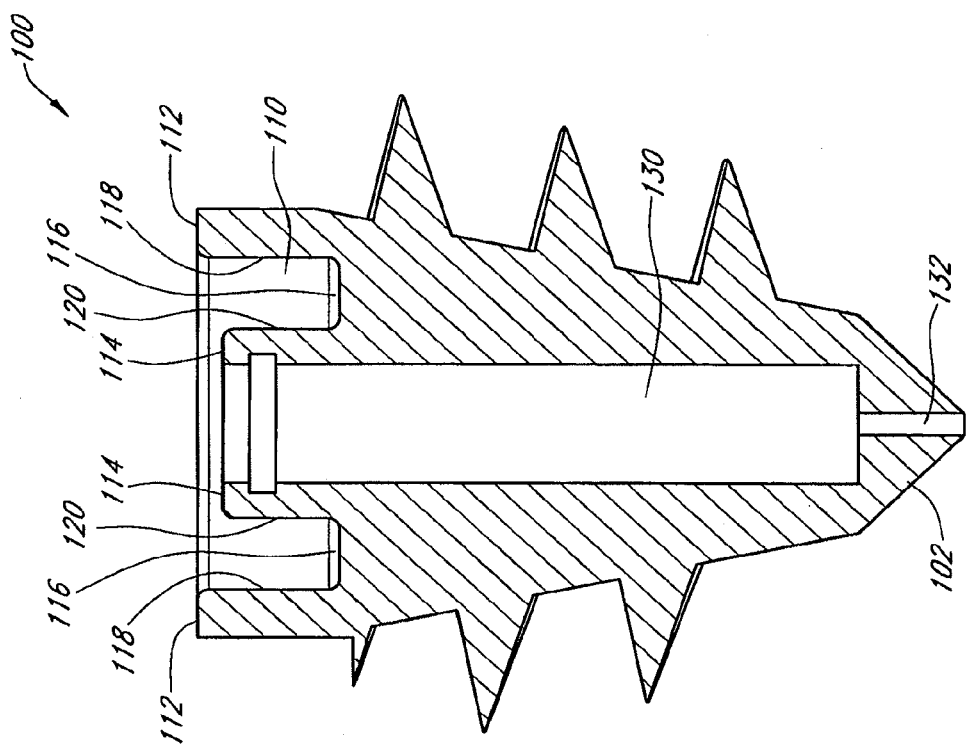
Figure 4C:
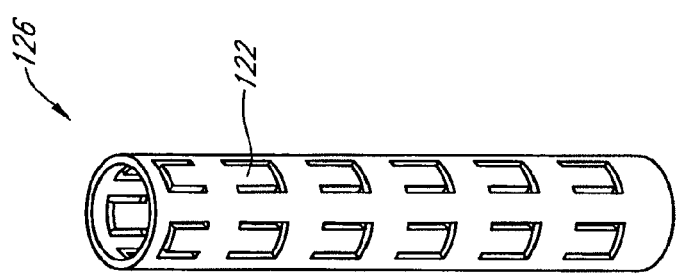

FIG. 4D depicts a cross section through the center of anchor base 100. This view illustrates central bore 130 and groove 110. The proximal surfaces 112, 114, 116, 118, and 120 are also apparent. Central bore 130 preferably does not extend all the way through the anchor base 100. Instead, a smaller bore 132 is present at the distal end 102 of the anchor base 100. Smaller bore 132 is used to receive a wire connected to an anchor inserter. It will be appreciated that other structures than bore 132 may be used for attaching the wire and that other means than a wire may be used to secure the anchor to the anchor inserter.

Figure 5B:
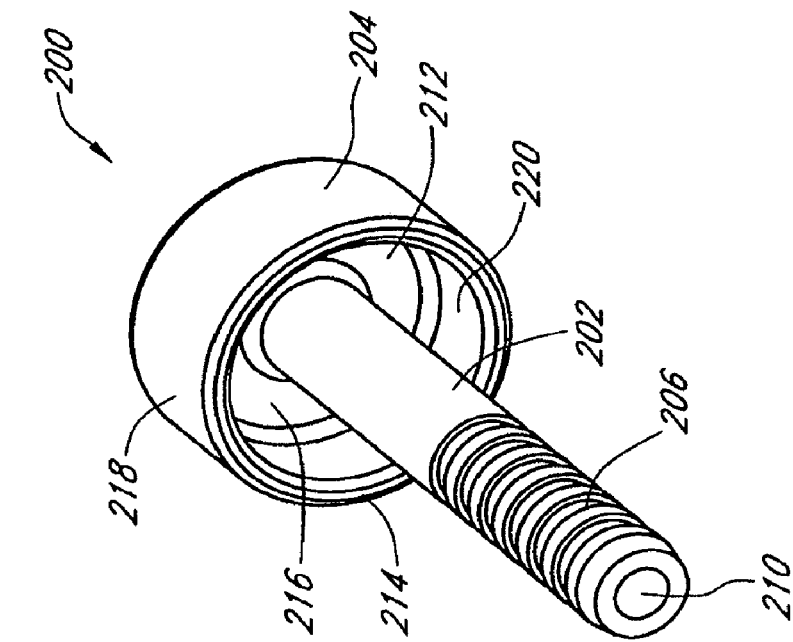
FIGS. 5A-5C depicts the top of a two-part suture anchor.
Figure 5A:
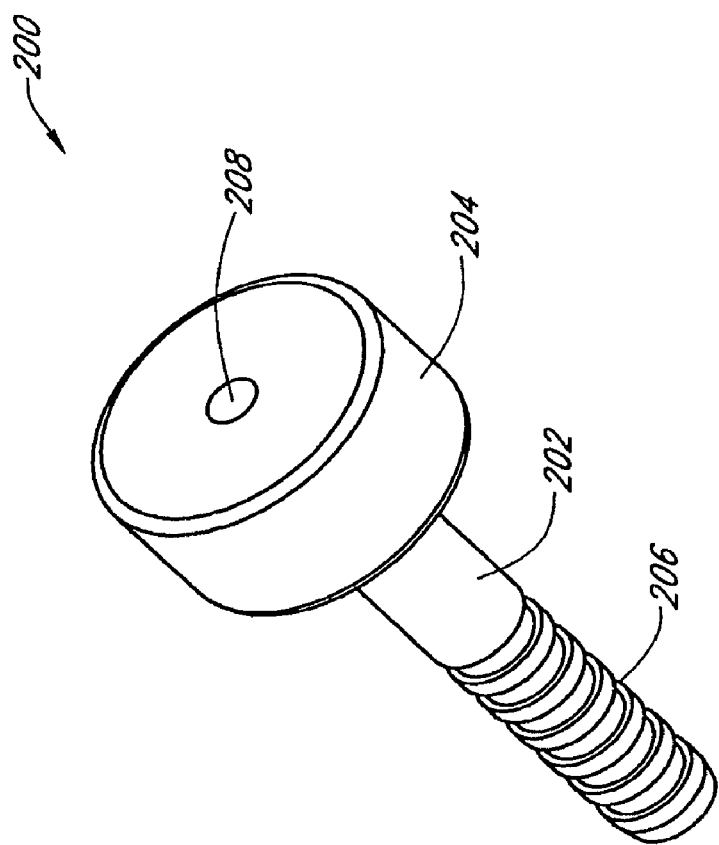
Figure 5C:
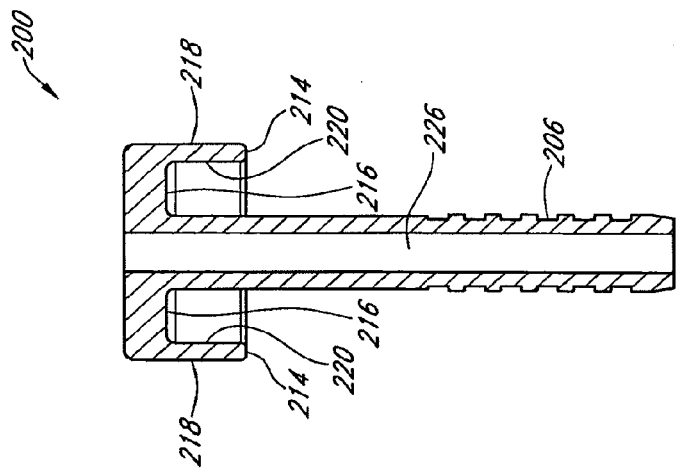

FIGS. 5A through 5C illustrate one embodiment of an anchor top 200. FIG. 5A provides a perspective view of the side and top of the anchor top 200 and FIG. 5B provides a perspective view of the side and bottom of the anchor top 200. Anchor top 200 has two members, a distal member 202 and a proximal member 204. The distal member 202 comprises an elongated shaft, the longitudinal direction of which shall be considered to run along the axis of the distal member 202. A series of grooves or other mating or locking surfaces or structures 206 exist along a portion of the outside surface of the shaft. The distal member 202 is designed to be inserted into the central bore 130 of the anchor base 100. The ratchet structures 122 in the anchor base 100 engage grooves 206 to couple the anchor top 200 to the anchor base 100. The ratchet structures 122 are oriented such that the distal member 202 can be easily moved in the distal direction in central bore 130 with the ratchet structures 122 snapping into the grooves 206 as the distal member 202 is moved downward. However, when the ratchet structures 122 are snapped into grooves 206, proximal movement of distal member 202 is inhibited. Thus, the anchor top 200 may be ratcheted down into anchor base 100. Because the ratchet structures 122 exist along substantially the entire surface of the central bore 130 (see FIG. 4C), the anchor top 200 may be coupled to the anchor base 100 in several positions. In other words, in one embodiment the anchor top 200 need not be ratcheted into the anchor base 100 as far as it will go for it to be secured to the anchor base 100.

The proximal member 204 of anchor top 200 is generally cylindrical in shape with a diameter larger than distal member 202. A hole 208 may advantageously be provided in the center of proximal member 204. With reference to FIG. 5B, the bottom of distal member 202 also contains a hole 210. Holes 208 and 210 open into a central bore through the anchor top 200. This central bore allows the wire referred to above to extend through the anchor top 200 to be secured to bore 132 in the anchor bottom 100, thus allowing the anchor bottom 100 to be attached to an anchor inserter while still allowing anchor top 200 to be ratchet into anchor bottom 100. FIG. 5B also illustrates that proximal member 204 contains a groove 212 in its distal surface. Thus, the distal surface of proximal member 204 is not flat and comprises distally facing surfaces 214 and 216 and side facing surfaces 218 and 220. In some embodiments, some or all of these surfaces may be textured such as with a scallop shape or grooves so as to inhibit movement of suture material pressed against the surfaces. In some embodiments, texturing in the distal surfaces of proximal member 204 match texturing in the proximal surfaces of anchor base 100. It will be appreciated that the illustrated embodiments represent only one possibility; thus, other shapes for the distal surface of proximal member 204 may also be used. FIG. 5C depicts a cross section through the center of anchor top 200. In this figure, the central bore 226 is depicted as are surfaces 214, 216, 218, and 220 and grooves 206.

Figure 6A:
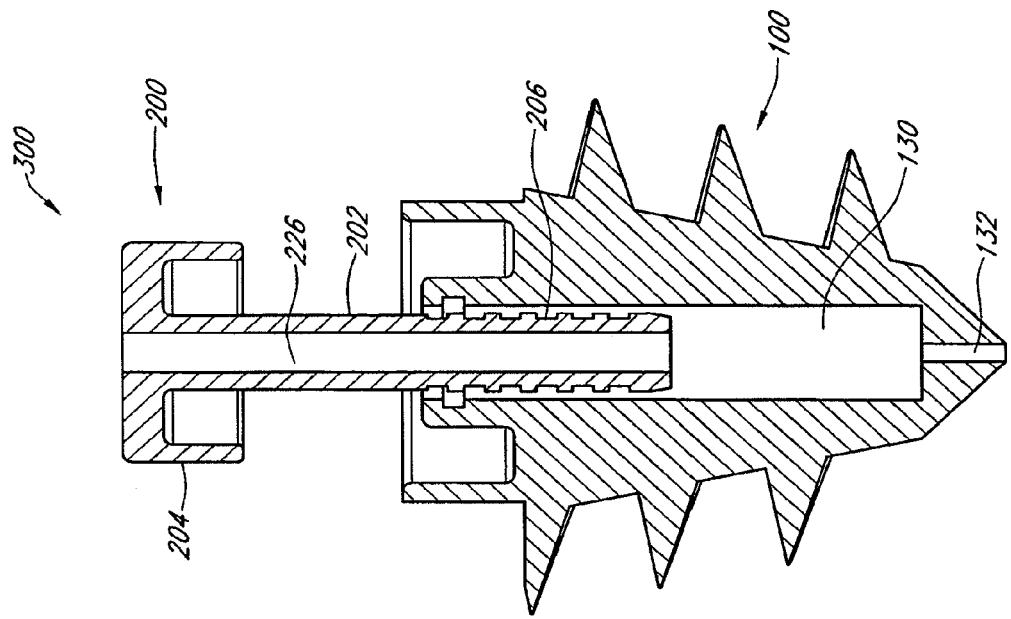
FIGS. 6A and 6B depict the suture anchor top of FIGS. 5A-5C inserted into the suture anchor bottom of FIGS. 4A-4D.
Figure 6B:
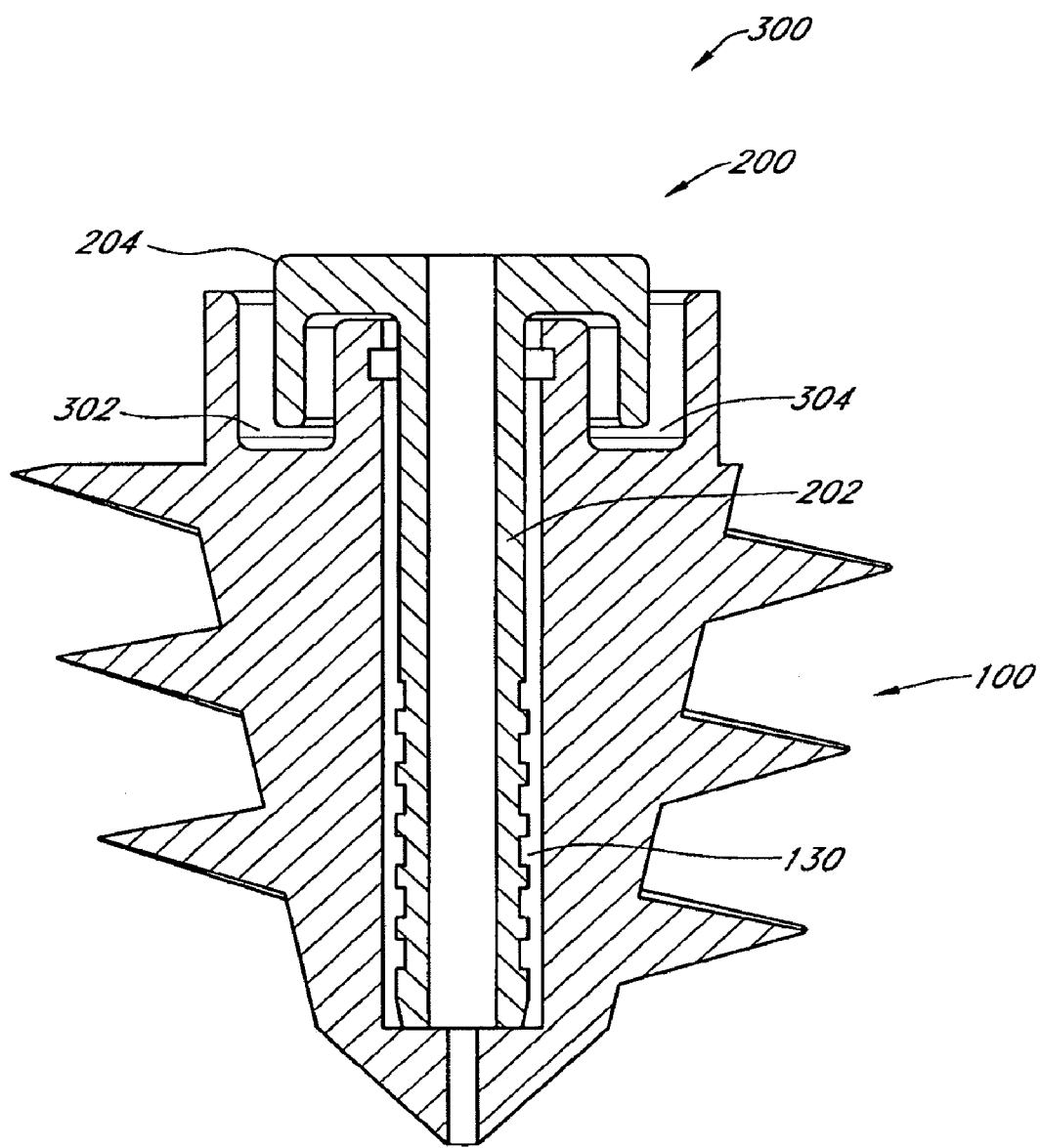

FIGS. 6A and 6B depict cross sections showing how the anchor top 200 may be coupled to anchor base 100 to form the complete anchor 300. In FIG. 6A, the anchor top 200 is coupled to anchor base 100 with the proximal member 204 separated from the anchor base 100. The anchor top 200 is secured to anchor base 100 by distal member 202 extending into central bore 130 of the anchor base 100. The distal member 202 is secured by ratchet structures (not shown) engaging grooves 206 in distal member 202. Central bore 226 in anchor top 200 and central bore 130 in anchor base 100 allow a wire to extend into the top of the anchor 300 and be secured to bore 132. Alternatively, the wire may be secured at other locations within central bore 130. Thus the wire, which can be coupled to an anchor inserter, can hold the entire anchor assembly 300 and still allow anchor top 200 to move relative to anchor base 100 and the wire.

FIG. 6B depicts the anchor assembly 300 with the distal member 202 of anchor top 200 ratcheted all the way into central bore 130 in anchor base 100. In this configuration, it can be seen that proximal surfaces 112, 114, 116, 118, and 120 of the anchor base 100 and distal surfaces 214, 216, 218, and 220 of the proximal member 204 of anchor top 200 form passageways 302 and 304. The size of passageways 302 and 304 are advantageously such that when a suture passes through them, it will be compressed so that it is securely attached to the anchor 300.

Figure 2:
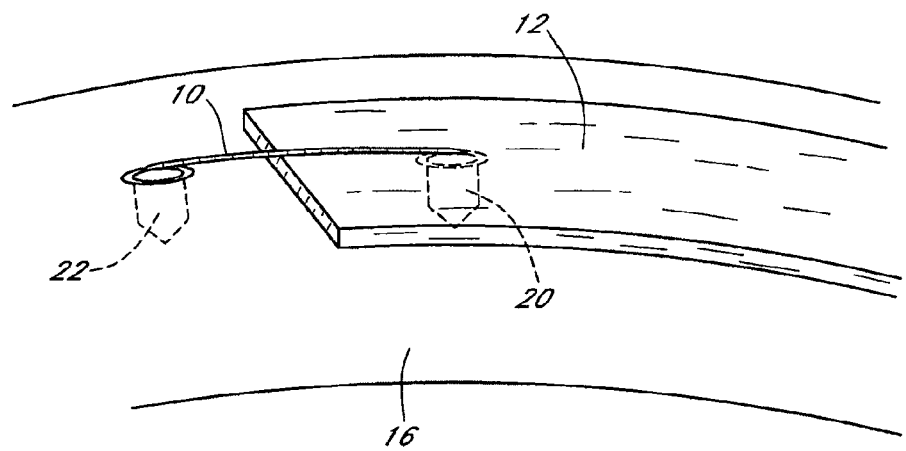

Another embodiment of the present invention is an inserter designed to insert and manipulate an anchor such as described in FIGS. 1-3. One such inserter 400 is depicted in FIGS. 7A and 7B. Inserter 400 comprises a handle 402 and an outer tube 404. As depicted in FIG. 7A, the handle 402 comprises a cover 403. FIG. 7B depicts the inserter 400 with cover 403 removed. Not depicted in FIGS. 7A and 7B are an inner tube disposed inside outer tube 404 and a wire disposed within the inner tube. As will be described in more detail below, the inner and outer tubes may be used to manipulate an anchor 300 such as that described in FIGS. 4-6. The wire may be used to couple the inserter 400 to the anchor 300 as described above. Inserter 400 also comprises an outer tube manipulator 406 and a wire manipulator 408. Outer tube manipulator 406 comprises release button 410. Outer tube manipulator 406 is securely attached to outer tube 404. Outer tube manipulator 406 may move longitudinally relative to handle 402 and the inner tube when release button 410 is pressed. Thus, when outer tube manipulator 406 is moved, outer tube 404 also moves.

Wire manipulator 408 comprises wire grabber 410 to which the wire is attached. The wire extends from wire grabber 410, through handle 402, and then through the inner tube. In one embodiment, wire manipulator 408 also comprises a release button 412. When release button 412 is pressed, the wire manipulator 408 may be pressed into the handle 402 to contact and thus provide additional tension on the wire. When in use, the additional tension causes the anchor base 100 to mover relative to inserter 400. When enough tension is provided to the wire by wire manipulator 408, the wire may break free from the anchor 300 at its attachment point in bore 132 or at some other predetermined location along the wire. It will be appreciated that any suitable breakable attachment means may be used for securing the wire to the anchor 300. For example, the wire may be frictionally secured into bore 132 or it may welded to the anchor base 100 using a weld that is weaker than the wire itself or a portion of the wire where breaking is desired may be weakened. In one embodiment, the wire is notched so as to create a weaker region in the wire that will break upon application of suitable force.

Figure 8:
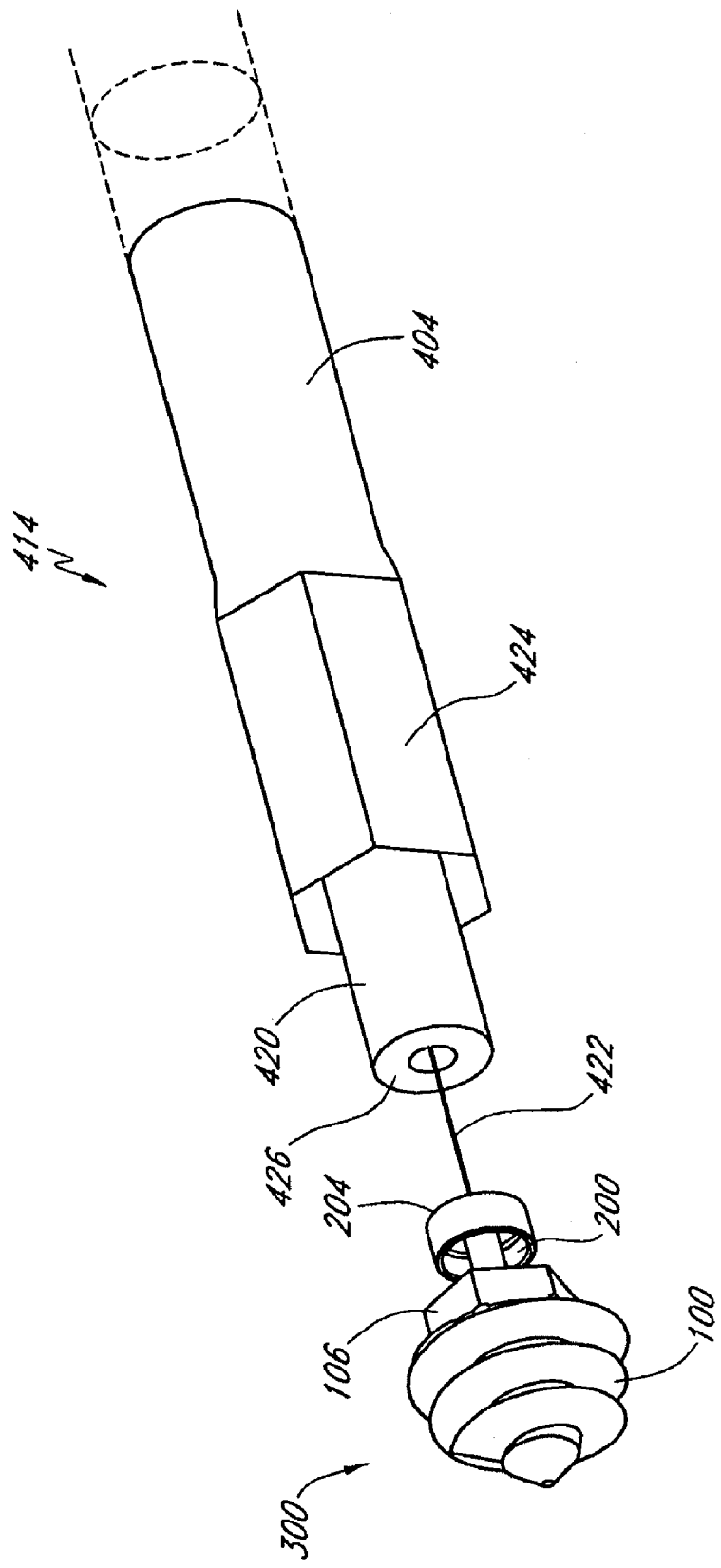
FIG. 8 depicts components on a suture anchor inserter for attaching to bone and manipulating a suture anchor.

The tip 414 of outer tube 404 is depicted in more detail along with inner tube 420, wire 422, and anchor 300 in FIG. 8. The end of outer tube 404 may comprise a hex nut driver structure 424 for receiving the hex nut structure 106 of anchor base 100. Of course, any other suitable engagement structure can be provided on the inserter 400 and the anchor base 100 in order to facilitate placement of the anchor base 100. Wire 422 extends out of inner tube 420 and into the central bore in the anchor top 200 to attach to anchor base 100 as described above. In some advantageous embodiments, the wire length and tension is adjusted such that the proximal member 204 of anchor top 200 buts against the end 426 of inner tube 420.

Figure 9A:
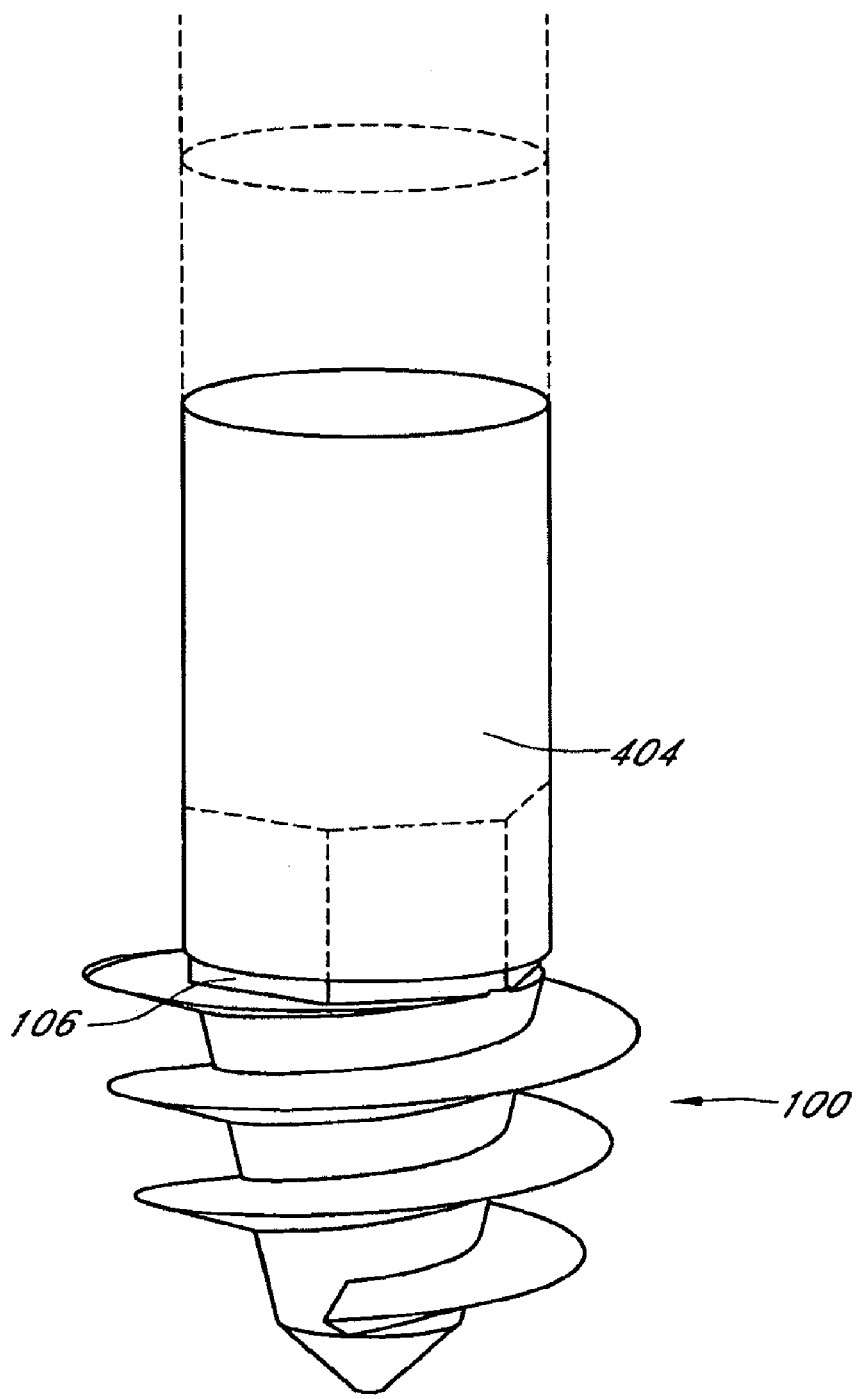
FIGS. 9A-9E depicts manipulation of a suture anchor using a suture anchor inserter to insert the suture anchor into bone and attach suture material to the suture anchor.

FIGS. 9A through 9E depict how inserter 400 and anchor 300 may be used to insert the anchor 300 into bone and attach a suture to it. FIG. 9A depicts the configuration for inserting the anchor 300 into bone. Outer tube 404 and outer tube manipulator 406 (see FIGS. 7A and 7B) are positioned relative to inner tube 420 and handle 402 (see FIGS. 7 and 8) so that the outer tube 404 engages hex nut structure 106 in the anchor base 100. It is advantageous in this configuration for the anchor top 200 to be in a position relative to the anchor base 100 such as depicted in FIG. 6A. In the configuration of FIG. 9A, a surgeon may then screw the anchor base 100 into bone by twisting handle 402 of inserter 400 (see FIGS. 7A and 7B).

Figure 9B:
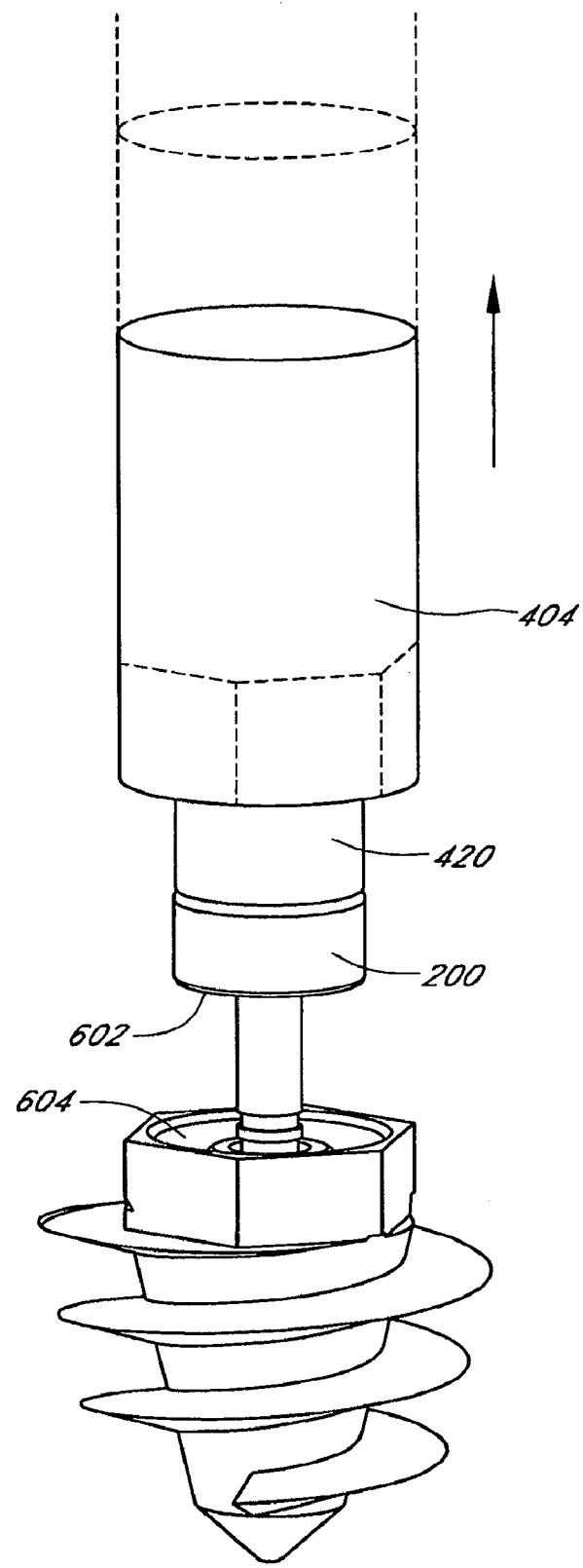
Figure 9C:
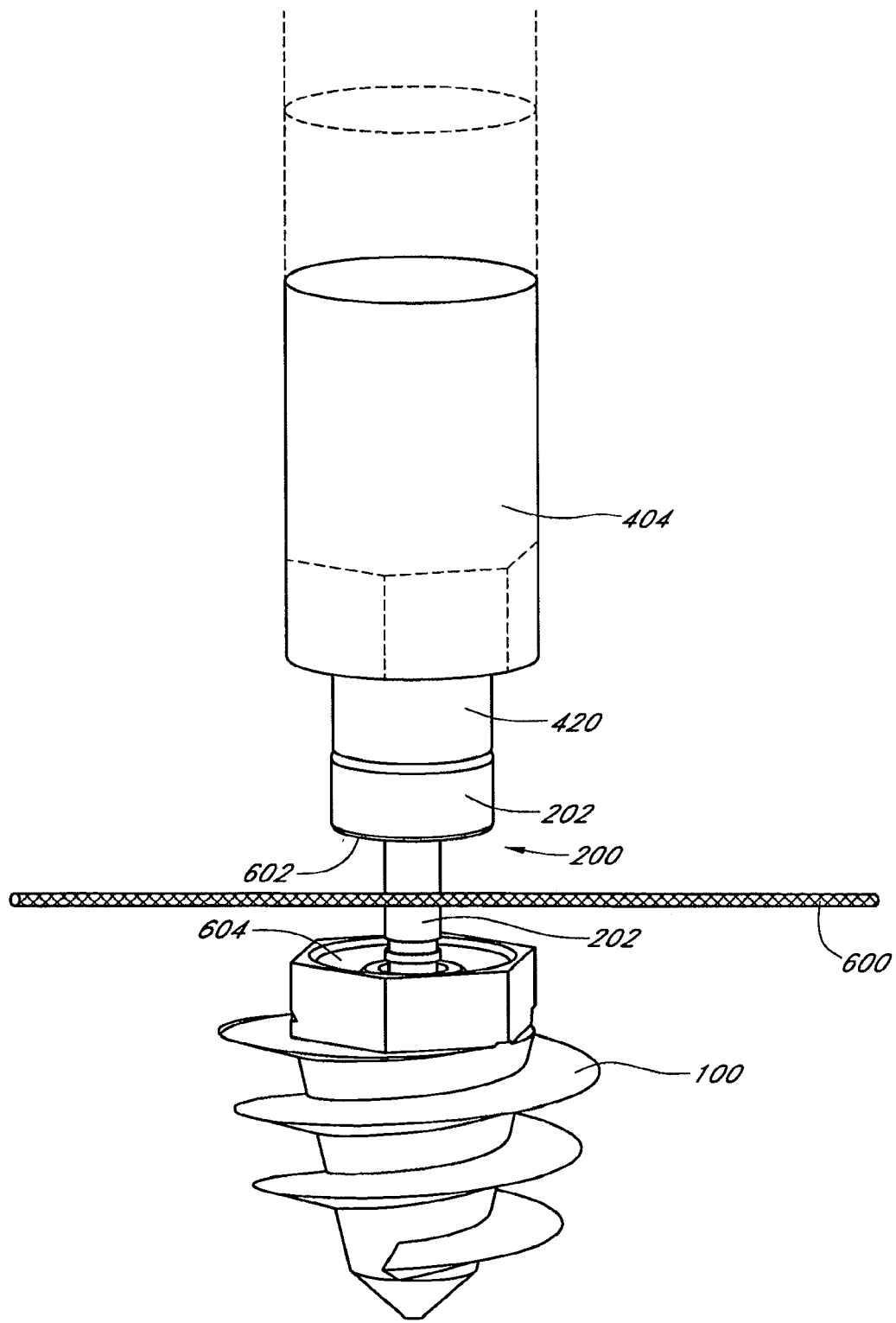

After the anchor base 100 is inserted into the bone, the outer tube 404 may be slid backward relative to the inner tube 420 and handle 402 to expose the anchor top 200 such as in FIG. 9B. One or more lengths of suture 600 may then be placed in the space between the distal surface 602 of the proximal member 204 of anchor top 200 and the proximal surface 604 of the anchor base 100 by moving the suture laterally into the space as depicted in FIG. 9C. The suture 600 may be manually tensioned as desired. In some embodiments, tensioning of the suture 600 is aided by pulling the suture 600 against the distal member 202 of the anchor top 200.

Figure 9D:
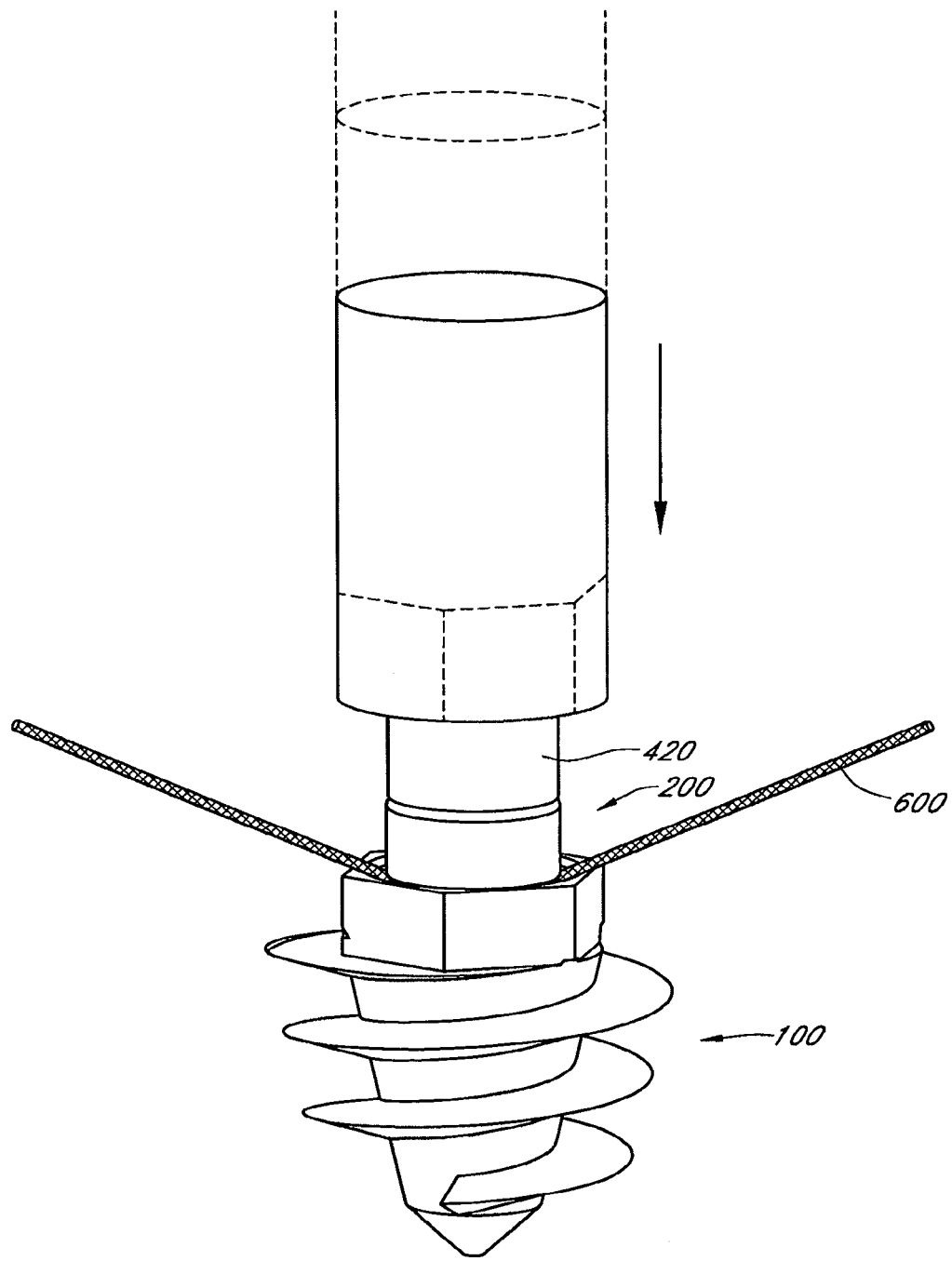
Figure 9E:
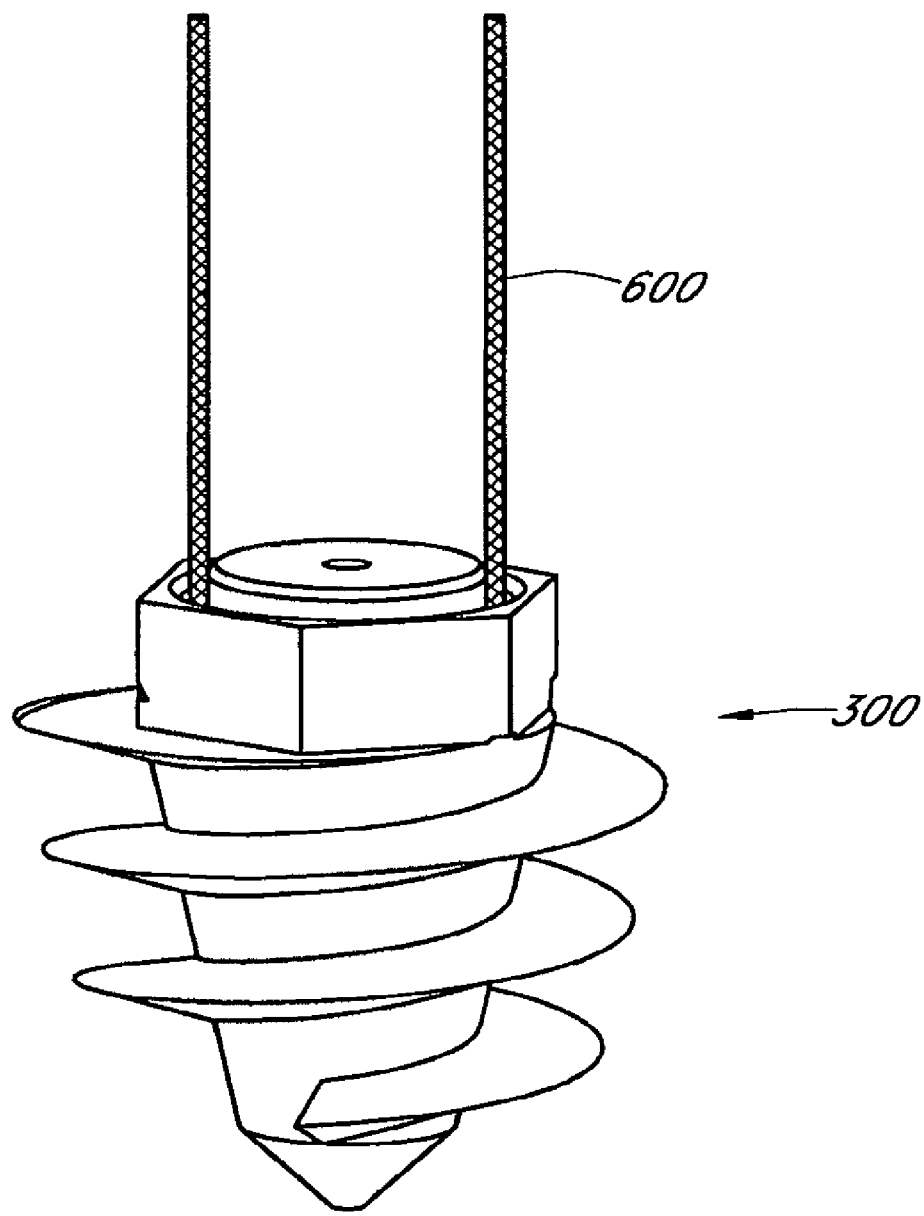

After appropriate tensioning of suture 600, wire manipulator 408 may be pressed to tension the wire, causing the handle 402 of the inserter 400 and the inner tube 420 to be pulled down towards the anchor base 100 so that inner tube 420 ratchets the anchor top 200 down into the anchor bottom 100 as depicted in FIG. 9D. As the anchor top 200 is pushed axially down, suture 600 will be clamped between the distal surface 602 of the proximal member 204 of anchor top 200 and the proximal surface 604 of the anchor base 100 (see also FIG. 9C). The clamping will force the suture to be compressed within the passageways 302 and 304 depicted in FIG. 6B and thus be secured to anchor 300. The fit between the anchor top 200 and the anchor base 100 in the clamping region is such that the suture 600 is firmly gripped, but is not cut, when it is clamped in place. Appropriate edges that may contact the suture are preferably beveled or rounded to avoid damage to the suture. After anchor top 200 is ratcheted sufficiently into anchor base 100, wire manipulator 408 (see FIGS. 7A and 7B) in inserter 400 may be compressed further to further tension wire 422 (see FIG. 8) such that wire 422 breaks free from its attachment to anchor base 100, thus leaving the anchor 300 free from inserter 400 with suture 600 securely attached as depicted in FIG. 9E.

Although a particular inserter device for inserting and manipulating anchor 300 has been described, it should be understood that other inserter designs may be used for manipulating the parts of anchor 300 described above to insert the anchor into bone and secure suture material to the anchor. For example, it may be possible to use separate tools for inserting the anchor and securing the suture material. In addition, in alternative embodiments, the anchor base 100 may be connected to the anchor top 200 throughout the procedure, or the anchor base may be separately inserted into the bone, and the anchor top can be attached thereafter by axially sliding the distal end of the anchor top 200 into the hole 108 in the anchor base 100.

It will be appreciated by those of skill in the art that the anchor 300 and inserter 400 provide a system for easy attachment of a suture to bone. The anchor 300 may be inserted into bone with minimal disruption of surrounding tissue. Only an access route having the diameter of the outer tube 404 and the anchor base 100 is required. Furthermore, the suture can be securely attached to the anchor 300 and tensioned as desired without having to insert additional instrumentation into the site or without performing any cumbersome attachment maneuvers such as knot tying. It should also be appreciated that the general principle illustrated by this system of inserting an anchor into bone without having suture material pre-attached and then attaching suture to the anchor without tying any knots may be implemented using any appropriate system other than the specific embodiments depicted in FIGS. 4-9.

Tissue and Bone Piercing Anchor

One embodiment is a bone anchor adapted for piercing through the soft tissue and into underlying bone. In one embodiment, the suture material may be pre-attached to the piercing bone anchor so that after implantation, a suture passes from the bone anchor through the top of the soft tissue for easy passing over the soft tissue. In one embodiment, the piercing bone anchor has two configurations, a first configuration having a small diameter for easy piercing through soft tissue and bone and a second deployed configuration where structures such as protrusions are deployed to prevent the bone anchor from being easily removed from the bone.

In one embodiment, the anchor includes a substantially hollow cylinder having a portion of its walls cut in such a manner so as to allow the cylinder to deform under axial stress and form lateral protrusions. The lateral protrusions may thus prevent the anchor from being easily removed from the bone after deployment. In one embodiment, the anchor comprises a pointed tip coupled to the hollow cylinder for piercing the soft tissue and bone. In one embodiment, suture is pre-attached to the pointed tip inside of the hollow cylinder. In other embodiments, suture is pre-attached at other locations on the piercing anchor, such as at the proximal end of the hollow cylinder.

Figure 10A:
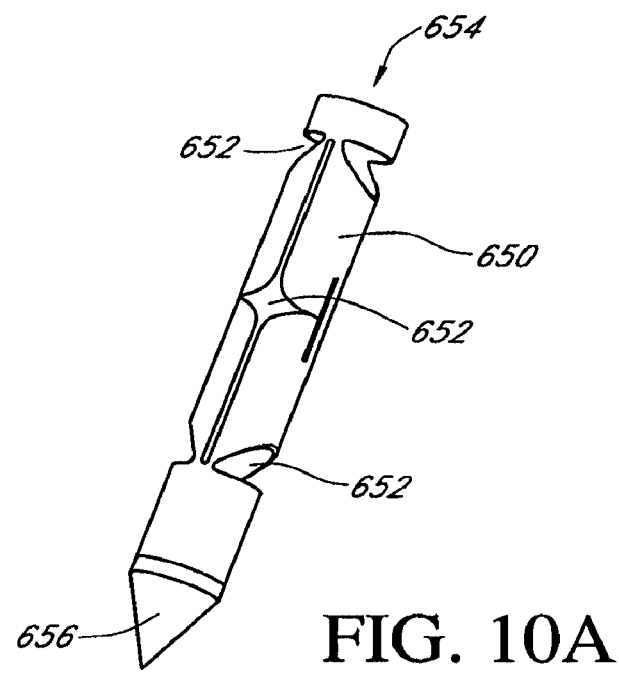
FIGS. 10A and 10B depict a piercing bone anchor in an un-deployed (FIG. 10A) and deployed (FIG. 10B) state.
Figure 10B:
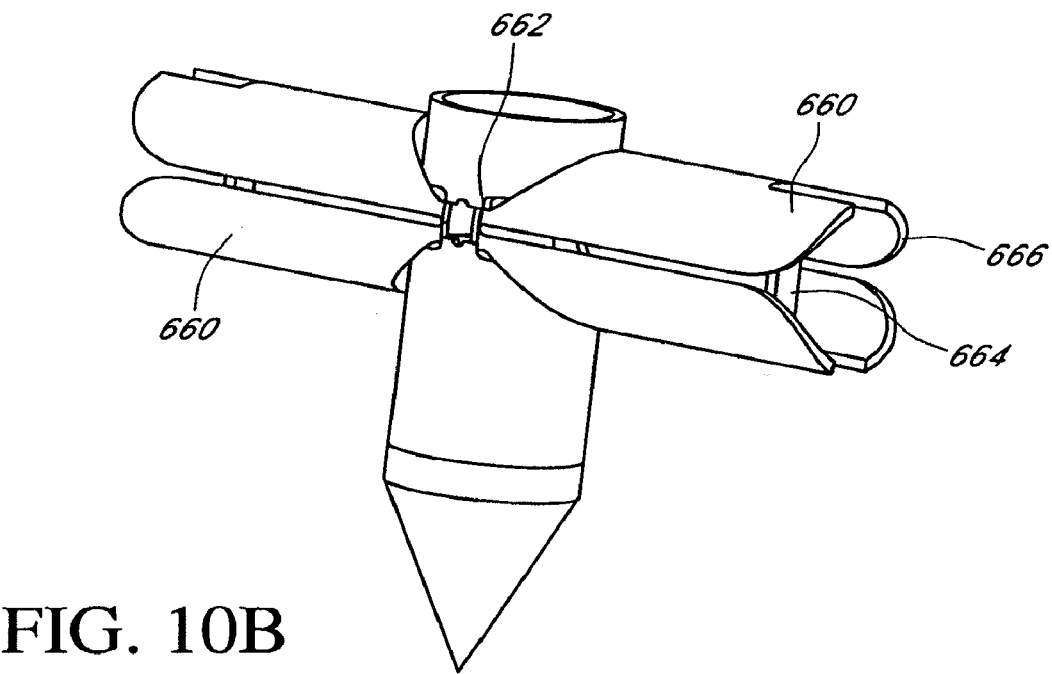

One embodiment of a deployable piercing anchor is depicted in FIGS. 10A and 10B. In FIG. 10A, the anchor is depicted in a pre-deployed state. The anchor includes a substantially hollow cylinder 650 with a plurality of cuts 652 in the side of the cylinder 650. The cylinder 650 is open on one end 654. On the other end, a pointed tip 656 is disposed, allowing the anchor to pierce through soft tissue and bone. In FIG. 10B, the anchor is depicted in a deployed state. Stress is applied in an axial direction such that the cylinder 650 collapses along cuts 652 so as to form two lateral wings 660. The lateral wings 660 prevent the anchor from being removed from the bone. Hinges 662 connect one end of each wing to either the top or the bottom parts of anchor body. These hinges deform and fold, in the plane tangent to the anchor body at that point when the anchor is deployed. A strip of material 664 connects the top and bottom wing on each side of the anchor body, and serves as a hinge between the two as well as aiding in alignment of the wings during deformation. The tips of the wings adjacent to the connecting strip 664 utilize rolling edges 666, which ensure uniform alignment and smooth transition during deformation. Those of skill in the art will appreciate that any number of geometries of cuts in the cylinder 650 may be utilized to create a deformable structure that will produce lateral protrusions upon exposure to stress.

Figure 11:
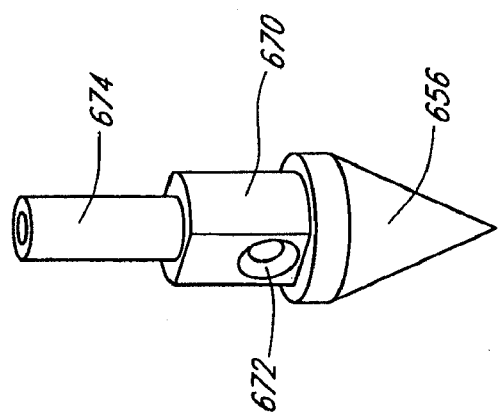
FIG. 11 depicts a piercing bone anchor tip.

In some embodiments, structures may be positioned within the cylinder 650 for attaching sutures and engaging with an anchor inserter. In one embodiment, such structures are coupled to the anchor tip 656 within the cylinder 650. FIG. 11 depicts one such embodiment. Attached to the tip 656 is a structure 670 through which there is an aperture 672. The structure 670 may be adapted to engage the inner surface of cylinder 650 for attaching the tip 656 to the cylinder 650. The attachment mechanism may be by forced fit, frictional fit, threads, welding, adhesive, or any other suitable means. Suture material may be threaded through the aperture 672 in order to attach the suture to the anchor. The suture material may be secured to the tip 656 by tying the suture around structure 670, tying a knot in the end of the suture that prevents it from being pulled through the aperture 672, clamping the suture between the structure 670 and the inside of the cylinder 650, adhering the suture to structure 670 by welding or adhesive, or any other suitable means. In one embodiment, the suture material is attached to the anchor at tip 656 prior to use of the anchor.

An anchor inserter attachment structure 674 may also be coupled to the tip 656. This structure 674 may couple to an anchor inserter through a wire or any other suitable means. The attachment between the anchor inserter and the anchor at this point may be used to apply axial stress to the anchor for deploying the anchor as described above. The attachment at this point may also serve to keep the anchor attached to the inserter prior to deployment.

Figure 12:
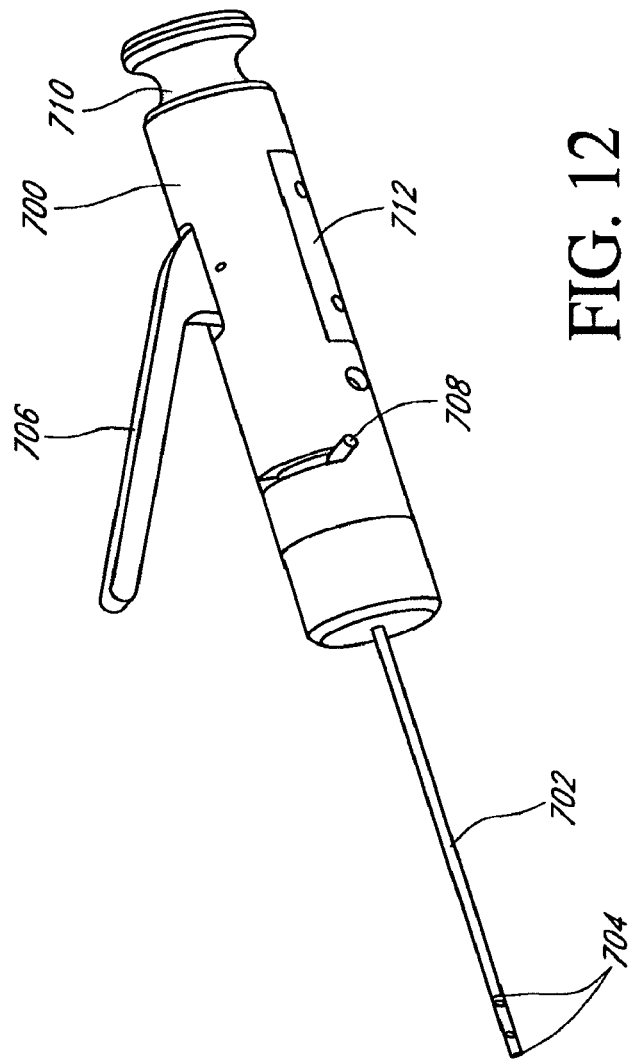
FIG. 12 depicts an anchor inserter for inserting a piercing bone anchor.

One embodiment of an anchor inserter suitable for use with the above-described anchor is depicted in FIG. 12. The anchor inserter comprises a grasping handle 700 to which is attached an outer sleeve 702 which is fixed relative to the handle 700. The piercing anchor 704 is disposed at the end of the sleeve 702. A deployment lever 706 may be pressed by a user to deploy and detach the anchor 704 as described below. A safety switch 708 may be provided to prevent the anchor 704 from being deployed prematurely. A spool 710 may be provided at the proximal end of the handle 700 for holding excess suture. A lid 712 may be provided for gaining access to the inner components of the inserter.

Figure 13:
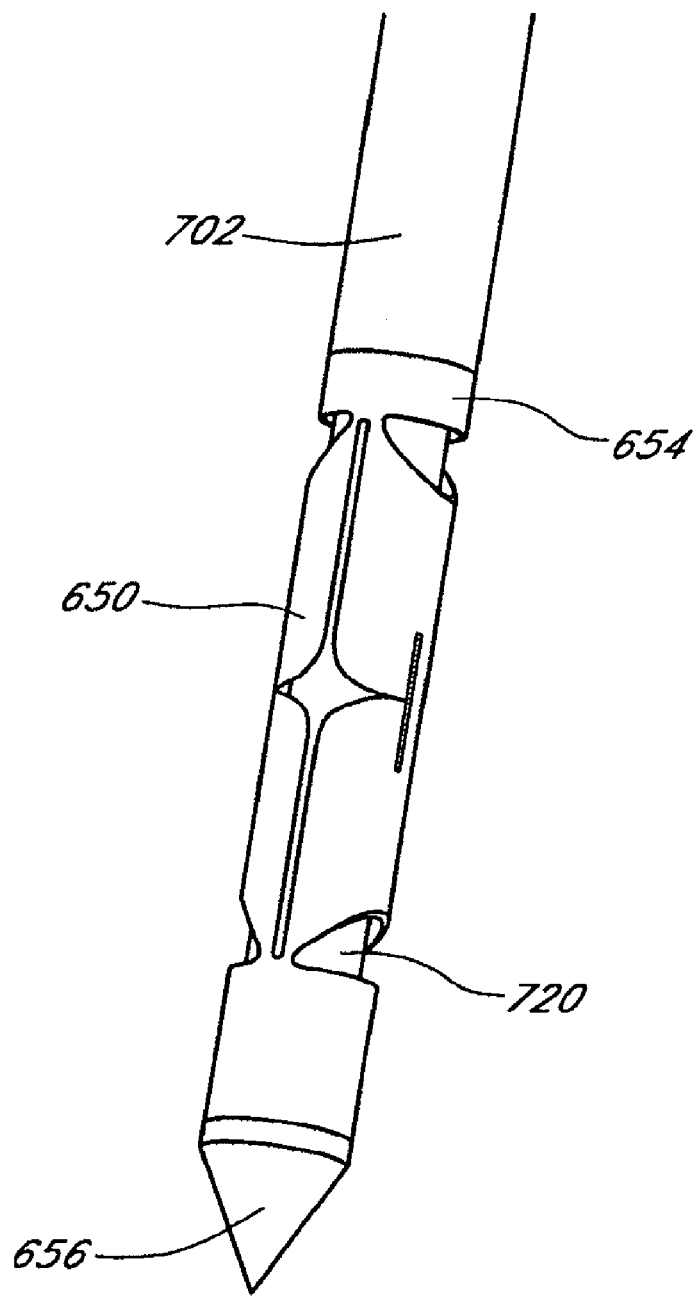
FIG. 13 depicts the interface between a piercing bone anchor and an anchor inserter.

FIG. 13 depicts the anchor 704 coupled to the inserter. As described above, the anchor 704 comprises a hollow cylinder 650 with cuts in the sides and a pointed tip 656. Furthermore, as depicted in FIG. 11, a suture receiving aperture 672 and an inserter attachment structure 674 are attached to the pointed tip 656 within the cylinder 650. The outer sleeve 702 of the inserter may fit over the open end 654 of the cylinder 650 or be flush with the open end 654. The outer sleeve 702 may thus hold the top part of the anchor 704 steady during insertion. In an alternative embodiment, the outer sleeve 702 may fit over the length of the cylinder 650 to prevent the cylinder 650 from deforming while it is being inserted into bone. In this alternative embodiment, the outer sleeve 702 may be retracted prior to deployment of the anchor. An inner tube 720 may be positioned within the outer sleeve 702 and the hollow cylinder 650 and contact the top surface of the anchor tip 656 (see FIG. 11). The inner tube 720 provides structural reinforcement of the anchor 704 and pushes against the tip of the anchor 704 while it is being driven into bone or tissue. The inner tube 720 may be fixed relative to the handle 712 and outer sleeve 702 during insertion, however, during deployment of the anchor 704, the inner tube 720 may be released by switching safety switch 708 so that the inner tube 720 can move axially relative to the outer sleeve 702 while the anchor cylinder 650 collapses. A wire may be positioned inside of the inner tube 720 running from within the handle 712 through the inner tube 720 to the anchor 704 and attached to the anchor inserter attachment structure 674. During deployment, the lever 704 may be pressed to pull the wire axially towards the handle 700. The axially movement of the wire forces the anchor 704 to press against outer sleeve 702 and stresses the cylinder 650, causing it to deform and deploy. During collapse of the cylinder 650, the inner tube 720 will also move in an axial direction toward the handle 700. Upon further stress on the wire, the wire may break free from the anchor inserter attachment structure 674, releasing the inserter from the anchor 704. Suture material may run from the inside of handle 700 through the inner tube 720 to attach to the anchor 704 through aperture 672 (see FIG. 11). Upon detachment of the anchor inserter from the anchor 704, the inserter may be withdrawn, leaving the inserted and deployed anchor with suture coming out of the open end 654 of the cylinder 650. The suture will still be coupled to the inserter through the inner tube 720, handle 700, and around spool 710. Those of skill in the art will appreciate other inserters and mechanisms that may be used to insert and deploy the piercing anchors described herein. For example, rather then axially stressing the anchor 704 by pulling the tip 656 in an proximal direction, the cylinder 650 may be pushed in a distal direction to deform the cylinder 650.

Figure 14:
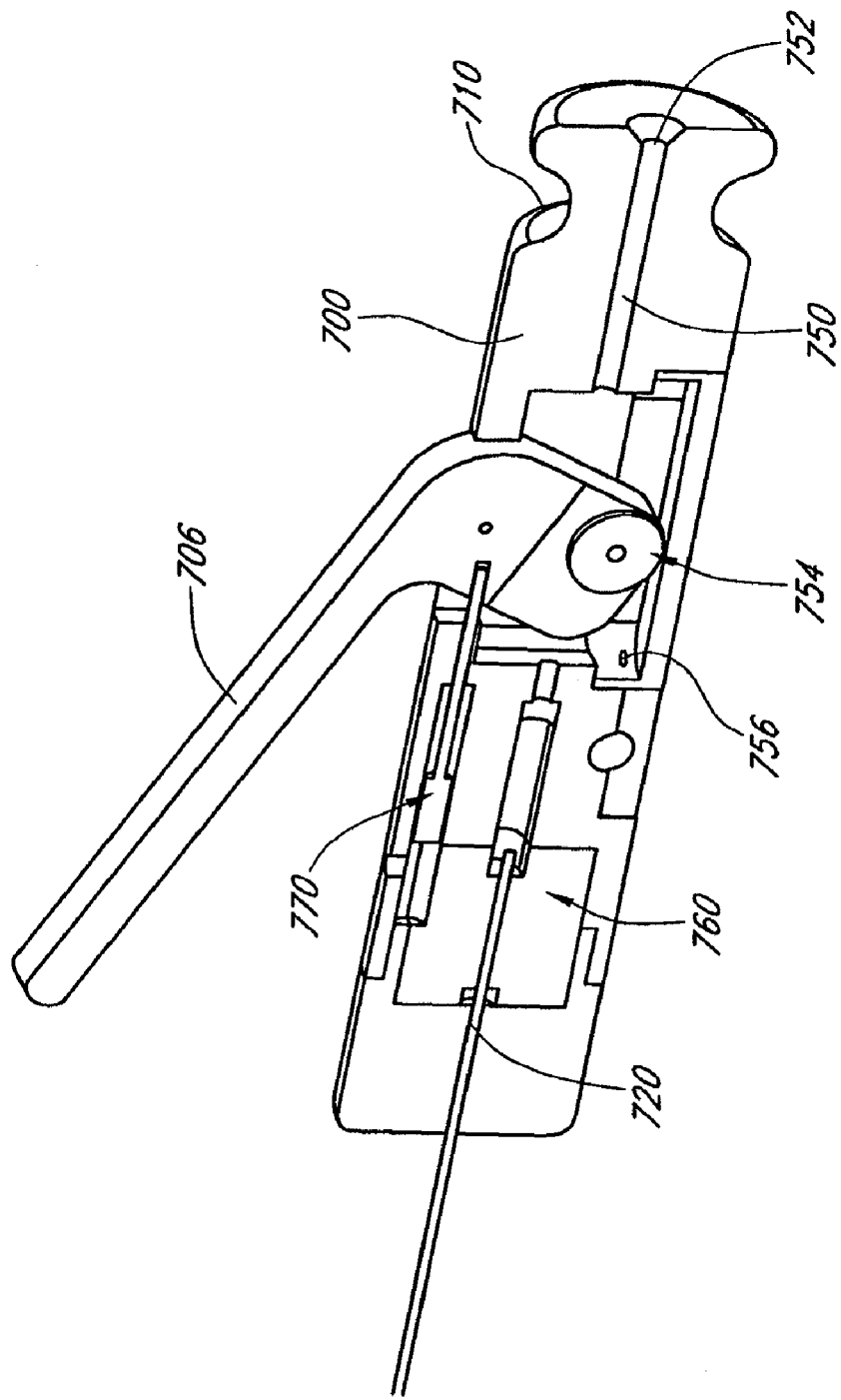
FIG. 14 is a cut-away view of a bone anchor inserter.

FIG. 14 is a cut-away view of the handle 700, showing the inner workings of the anchor inserter. The suture material attached to a piercing anchor at the tip of the inserter may pass through the central bore of the inner tube 720 and through a bore 750 in the handle 700. The suture material may then pass through a hole 752 in the end of the handle 700 and be wrapped around the spool 710, which may be integral with the handle 700. The wire attached to the anchor inserter attachment structure 674 in the anchor may also pass through the central bore of the inner tube 720 and may then proceed around a pulley 754 and attach securely to the handle 700 at point 756. The pulley 754 may be attached to the lever 706. When the lever 706 is pressed down, the pulley 754 will move toward the back end of the handle 700, causing the wire attached to the anchor to retract. Because of the use of pulley 754, the wire will retract twice the distance as the pulley 754 moves.

Figure 15:
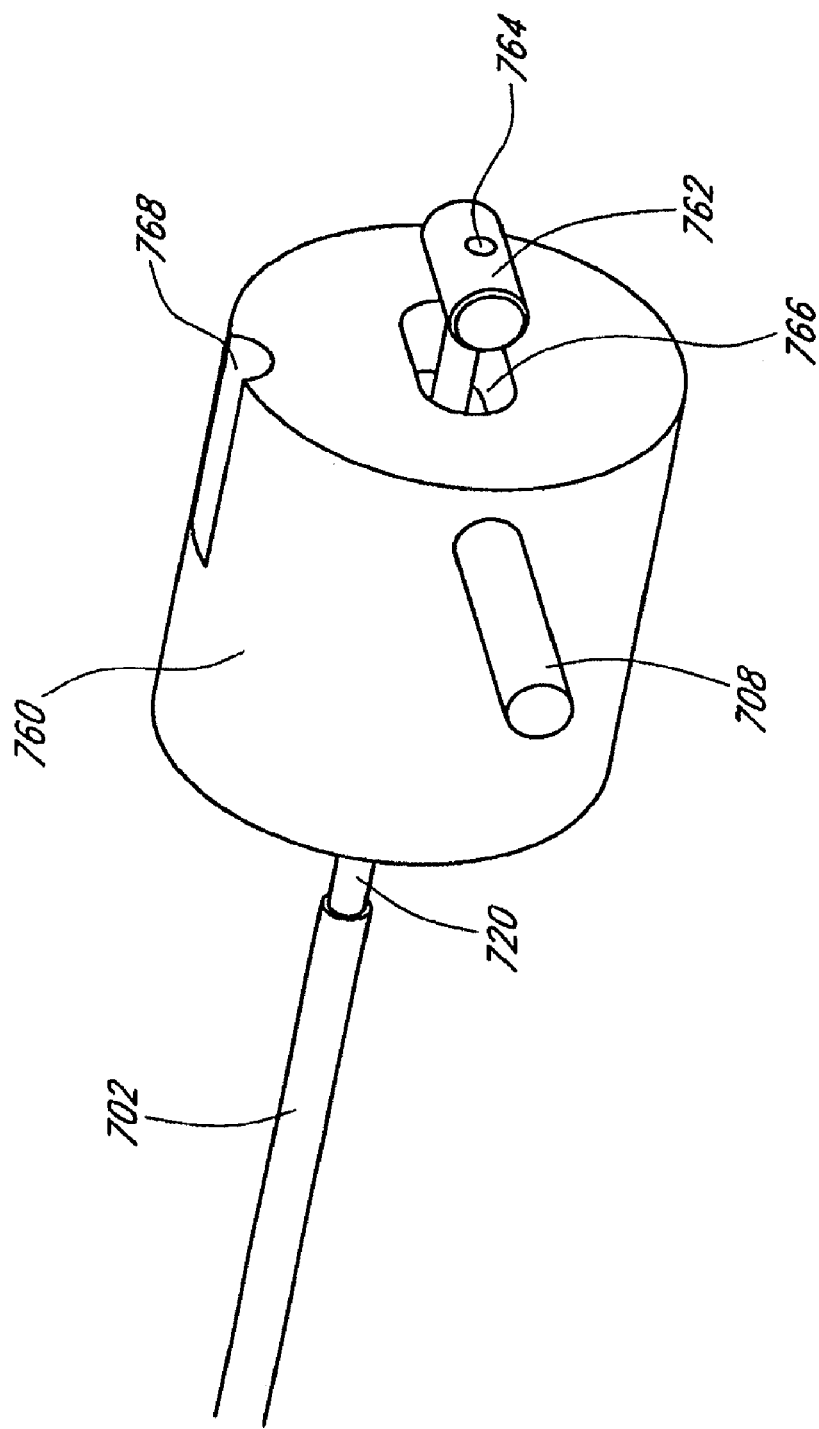
FIG. 15 depicts a safety switch mechanism for a bone anchor inserter.

The safety switch 708 may be used to prevent the lever 706 from being pressed and prevent the inner tube 720 from moving unless the safety switch 708 is in the correct position. The safety mechanism operates via a drum 760 disposed within the handle 700 to which the safety switch 708 is attached. Moving the safety switch 708 rotates the drum 760 within the handle 700. FIG. 15 shows the drum 760 and safety switch 708 mechanism in more detail. The inner tube 720 passes through a central bore in the drum 760. On the other side of the drum 760, the inner tube 720 is attached to a stopper 762. The stopper 762 has a through-hole 764 to permit passage of the deployment wire and suture. The stopper 762 may be positioned within a cavity 766 in the end of the drum 760. A second similarly shaped cavity may be disposed within the handle 700. The stopper 762 and attached inner tube 720 may only be allowed to move axially relative to the handle 700 when the safety switch 708 and drum 760 is rotated so that the cavity 766 in the drum 760 is aligned with the matching cavity in the handle 700. When the cavities are aligned, the stopper 762 is allowed to move from the cavity 766 to the cavity in the handle 700, thus allowing the inner tube 720 to move axially and the anchor to be deployed.

Additionally, the drum 760 comprises a groove 768. A spring-loaded sliding pin 770 (see FIG. 14) may be coupled to the lever 706. The lever 706 can only be moved when the drum 760 and switch 708 are rotated so that groove 768 is aligned with the pin 770. Thus, both the stopper 764 and the pin 770 prevent the anchor from being deployed unless the switch 708 is in the correct position.

Those of skill in the art will appreciate other mechanisms that could be used for deploying a deployable anchor and providing safety mechanisms to prevent premature deployment.

Example Using a Piercing Anchor and a Suture Capturing Anchor

Figure 16A:
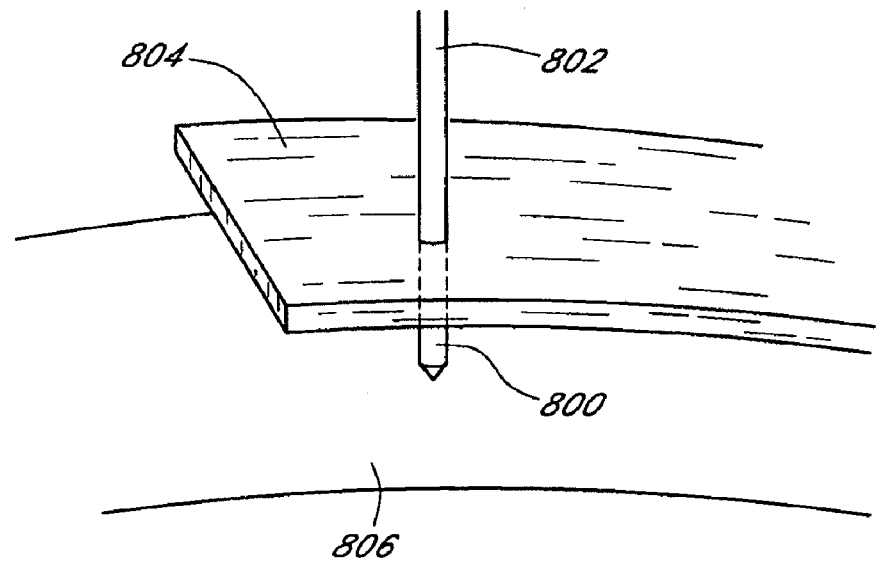
FIGS. 16A-16F depict a method for attaching soft-tissue to bone using a piercing bone anchor and a suture capturing anchor.
Figure 16B:
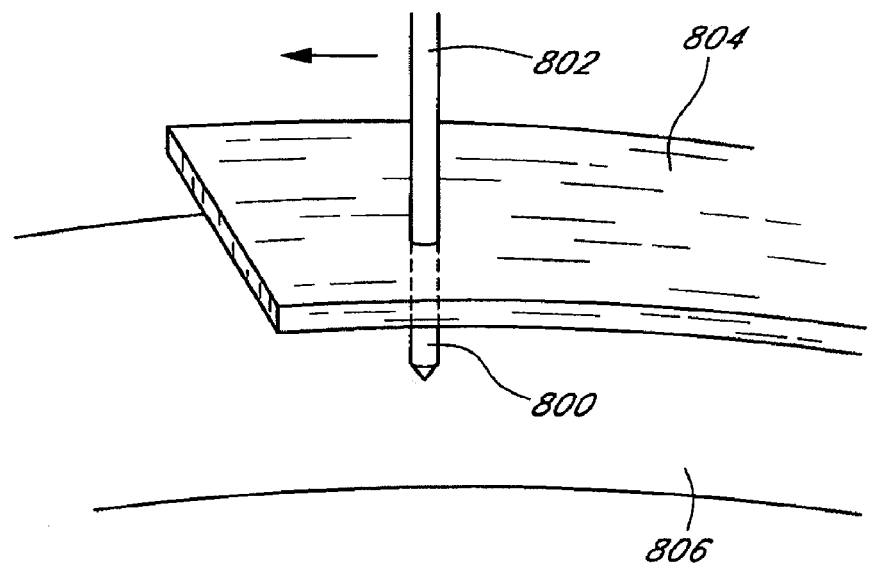
Figure 16C:
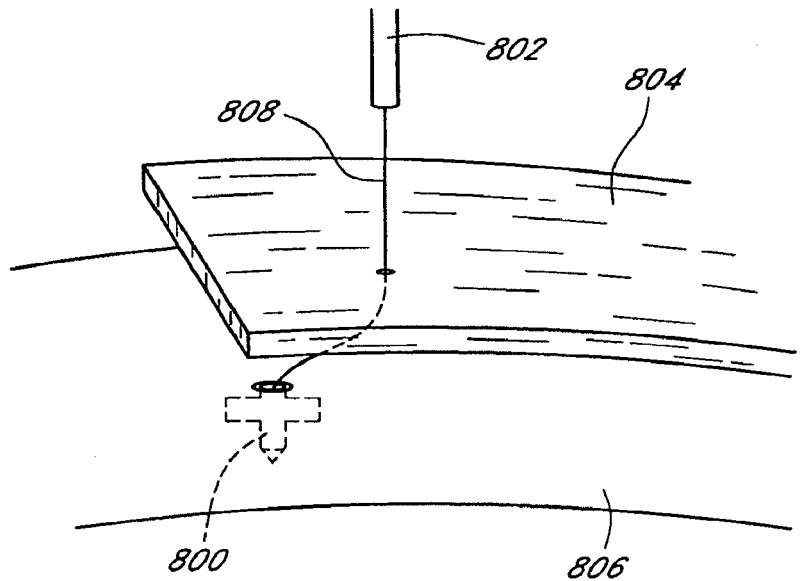

The above-described anchors may be used in a surgical procedure for attaching soft tissue to bone. One example of such a procedure is depicted in FIGS. 16A through 16F. In FIG. 16A, the piercing anchor 800 attached to an anchor inserter 802 as described above is pierced through soft tissue 804 that has become detached from underlying bone 806. In FIG. 16B, the anchor inserter 802 is moved laterally relative to the bone 806 so as to stretch the soft tissue 804 laterally relative to the bone 806. Once the soft tissue 804 has been stretched to the desired position, the anchor 800 is inserted into the bone 806 and the anchor 800 is deployed as described above and the inserter 802 is detached from the anchor 800, leaving a suture 808 attached to the anchor 800 and extending through the soft tissue 804. The anchor 800 may be inserted into bone 806 by tapping on the inserter 802 with a hammer or by any other suitable means of applying axial force. FIG. 16C depicts the deployed anchor 800 with attached suture 808. The suture 808 will extend into the inserter 802.

Figure 16D:
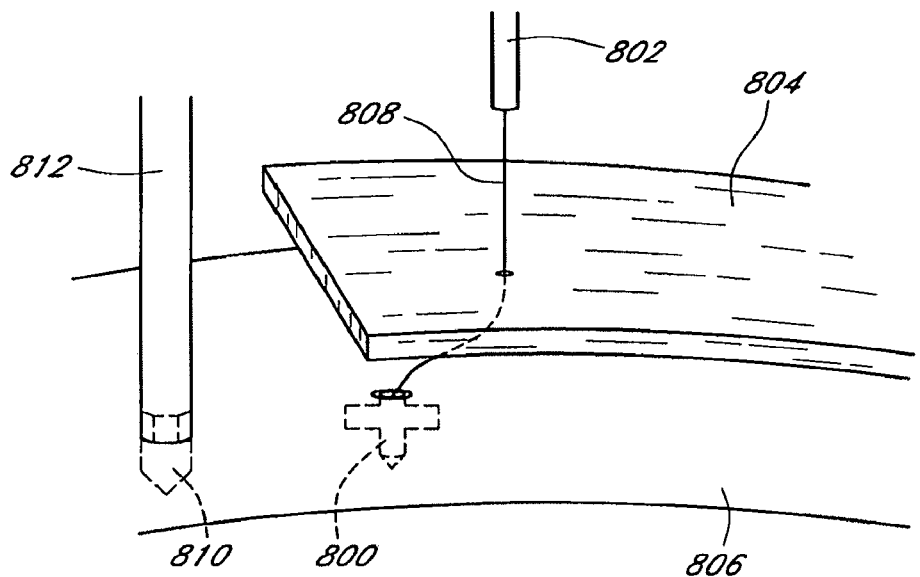
Figure 16E:
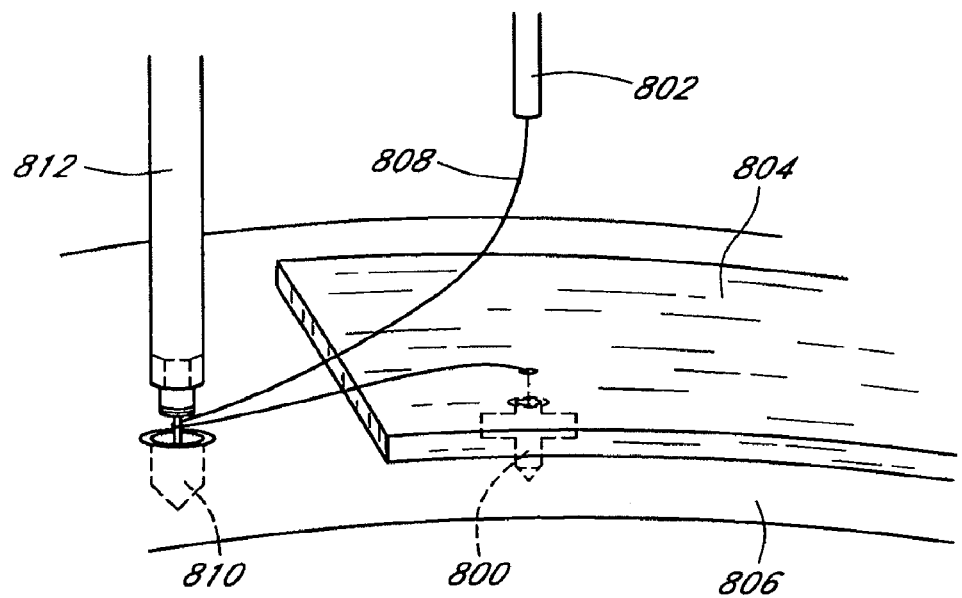
Figure 16F:
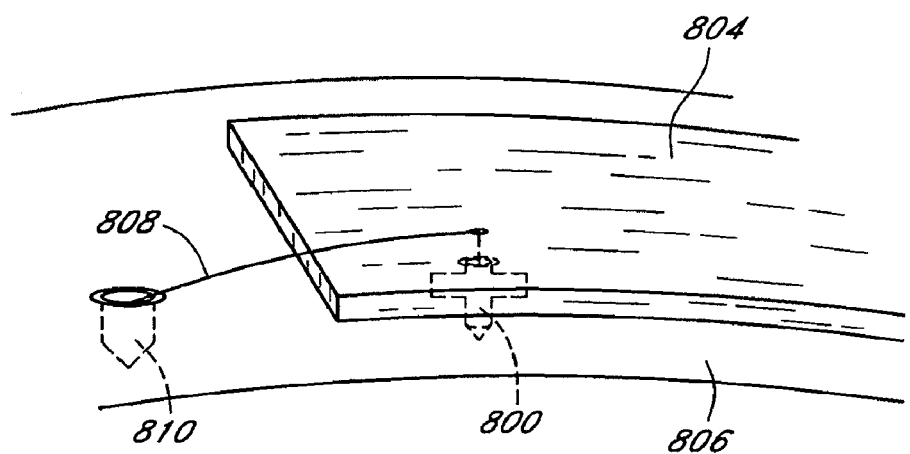

Next, as depicted in FIG. 16D, a suture capturing anchor 810 is inserted into the bone 806 using the inserter 812 as described above. In FIG. 16E, the inserter 812 is then retracted to expose the suture capturing mechanism. The suture 808 is then passed over the soft tissue 804 and laterally moved into the suture capturing mechanism and tensioned. Finally, as depicted in FIG. 16F, the suture capturing mechanism is deployed to capture the suture 808, the anchor inserter 812 is detached from the anchor 810, and the suture 808 is cut to detach it from the suture inserter 802. The result is a length of suture 808 between the bone anchors 808 and 810 that presses the soft tissue 804 against the bone 806. Multiple anchors and sutures may be used to produce geometries such as depicted in FIGS. 2 and 3 and variations thereof.

It will be appreciated that there are numerous stitches, suture threading patterns, and anchor patterns that may be used to secure soft tissue to bone by the methods and devices described herein. These variations as well as variations in the design of the above described anchor devices and inserter devices are within the scope of the present disclosure.

Methods of Attaching Soft Tissue to Bone

Various embodiments include methods for attaching soft tissue to bone. In some embodiments, the methods include using the bone anchors described above. In one embodiment, a bone anchor is inserted into the bone and then a length of suture is passed over the soft tissue and secured to the anchor after inserting the anchor without tying any knots or without passing the suture through an aperture in the anchor. In some embodiments, the suture is secured to the anchor by laterally moving it into a securing mechanism. In one embodiment, securing the suture to the anchor includes clamping the suture between at least two surfaces on the anchor. In one embodiment, the anchor is not inserted further into the bone after securing the suture to it.

In another embodiment, a first anchor with a suture pre-attached is inserted through the soft tissue and into the bone. The suture may then be passed over the soft tissue and fixedly secured to a second bone anchor. In one embodiment, the first anchor is inserted by directly piercing the soft tissue and the bone. In one embodiment, lateral protrusion may be deployed on the first anchor to prevent the first anchor from being removed. In one embodiment, the suture may be coupled to the second bone anchor prior to insertion and then fixedly secured after insertion. In this context, "coupled" means that the suture is attached to the bone anchor but not fixedly secured, such that the suture can move to some extent relative to the bone anchor. In an alternative embodiment, the suture is not coupled to the second bone anchor during its insertion.

In another embodiment, a first portion of suture is inserted into the proximal surface of the soft tissue. A second portion of the suture (e.g., the portion proximal to the inserted portion) is then passed over the proximal surface of the soft tissue and fixedly secured to a bone anchor. In one embodiment, the procedure may be performed without passing the first portion of the suture back out of the proximal surface of the soft tissue. In one embodiment, this result is accomplished by the first portion of the suture being attached to an anchor that is inserted through the soft tissue and into bone.

One embodiment includes inserting a first anchor with a pre-coupled suture through soft tissue and into bone. The suture may then be passed over the soft tissue and fixedly secured to a second anchor. In one embodiment, the pre-coupled suture is fixedly secured to the first anchor prior to insertion. In an alternative embodiment, the pre-coupled suture can move relative to the first anchor prior to insertion and is fixedly secured after insertion.

In another embodiment, multiple lengths of suture are attached to multiple anchors. In one embodiment at least three anchors are inserted into bone. A first length of suture may be secured between a first and second anchor and a second length of suture may be secured between the first and a third anchor. In one embodiment, the first anchor is positioned beneath the soft tissue and the second and third anchors are positioned laterally to the soft tissue. In an alternative embodiment, the first anchor is positioned laterally to the soft tissue and the second and third anchors are positioned beneath the soft tissue. In some embodiments, the lengths of suture are fixedly secured to the anchor(s) positioned beneath the soft tissue prior to insertion of those anchor(s). In one embodiment, the different lengths of suture may be tensioned separately.

In various embodiments, prior to fixedly securing suture to a bone anchor, it can be tensioned. In one embodiment, tensioning is accomplished by manually pulling on the suture such as by a surgeon grasping the suture using an appropriate instrument and then pulling. In one embodiment, the suture may be pressed against the bone anchor to provide leverage for pulling. For example, the suture may be wrapped partly around a proximal portion of the anchor prior to pulling.

Although the invention has been described with reference to embodiments and examples, it should be understood that numerous and various modifications can be made without departing from the spirit of the invention. Accordingly, the invention is limited only by the following claims.

What is claimed is:

1. A method of attaching soft tissue to bone, comprising:
    inserting a first anchor into bone, wherein after insertion, the first anchor is positioned underneath the soft tissue;
    passing a first length of suture from said first anchor over the soft tissue;
    inserting at least a portion of a second anchor into bone at a position beyond an edge of the soft tissue;
    after inserting said at least a portion of the second anchor, tensioning the first length of suture to compress an area of tissue to bone between the edge of the soft tissue and the first anchor; and
    after tensioning the first length of suture, fixedly securing the first length of suture at the second anchor position without tying any knots;
    wherein at least one of said anchors comprises an anchor tip and a hollow cylinder, wherein the anchor tip comprises an aperture through which suture material is threaded prior to insertion of the at least one anchor.

2. The method of claim 1, wherein said anchor tip comprises an engaging member adapted to engage an inner surface of said cylinder.

3. The method of claim 1, wherein said anchor tip comprises an anchor inserter attachment member.

4. The method of claim 3, wherein insertion of the at least one anchor comprising an anchor tip and a hollow cylinder comprises using an inserter that comprises a handle, an outer sleeve, and an inner member, wherein the inner member extends through the outer sleeve and the hollow cylinder and is attached to the anchor inserter attachment member.

5. The method of claim 4, wherein the inserter comprises an inner tube extending through the outer sleeve and through the hollow cylinder and contacts the anchor tip, wherein the inner member extends through the inner tube.

6. The method of claim 5, wherein the inner tube is fixed relative to the handle.

7. The method of claim 5, wherein the inner tube is movable axially relative to the outer sleeve.

8. The method of claim 5, wherein suture material runs from inside the handle of the inserter, through the inner tube, and through the aperture in the anchor tip.

9. The method of claim 8, wherein the suture material runs through a bore in the handle and passes through a hole in an end of the handle.

10. The method of claim 9, wherein the handle comprises a spool at a proximal end of the handle adapted to hold excess suture.

11. The method of claim 10, wherein the suture material is wrapped around the spool.

12. The method of claim 11, wherein the spool is integral with the handle.

13. The method of claim 4, wherein insertion of the at least one anchor comprising an anchor tip and a hollow cylinder comprises tapping on the inserter with a hammer.

14. The method of claim 1, comprising coupling the first length of suture to the at least one anchor comprising an anchor tip and a hollow cylinder prior to inserting the at least one anchor comprising an anchor tip and a hollow cylinder.

15. The method of claim 1, wherein the tensioning comprises manually pulling on the first length of suture.

16. The method of claim 1, comprising:
inserting a third anchor into bone, wherein after insertion, the third anchor is positioned underneath the soft tissue;
passing a second length of suture from said third anchor over the soft issue;
tensioning the second length of suture independently from the first length of suture; and
after tensioning the first and second lengths of suture, fixedly securing both the first and second lengths of suture at the second anchor position without tying any knots.

17. A method of attaching soft tissue to bone, comprising:
inserting a first anchor into bone, wherein after insertion, the first anchor is positioned underneath the soft tissue;
passing a first length of suture from said first anchor over the soft tissue;
inserting at least a portion of a second anchor into bone at a position beyond an edge of the soft tissue;
after inserting said at least a portion of the second anchor, tensioning the first length of suture to compress an area of tissue to bone between the edge of the soft tissue and the first anchor; and
after tensioning the first length of suture, fixedly securing the first length of suture at the second anchor position without tying any knots;
wherein at least one of said anchors comprises an anchor tip and a hollow cylinder, wherein the anchor tip comprises:
an aperture through which suture material is threaded prior to insertion of the at least one anchor,
an engaging member adapted to engage an inner surface of said cylinder, and
an anchor inserter attachment member, wherein insertion of the at least one anchor comprising an anchor tip and a hollow cylinder comprises using an inserter that comprises a handle, an outer sleeve, and an inner member, wherein the inner member extends through the outer sleeve and the hollow cylinder and is attached to the anchor inserter attachment member.

* * * * *